United States Patent
Hason et al.

(10) Patent No.: US 10,070,932 B2
(45) Date of Patent: Sep. 11, 2018

(54) SYSTEM AND METHOD FOR MANEUVERING COILS POWER OPTIMIZATION

(71) Applicant: GIVEN IMAGING LTD., Yoqneam (IL)

(72) Inventors: Eshel Hason, Yoqneam Ilit (IL); Golan Inbar, Kiryat Bialik (IL); Dori Peleg, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 219 days.

(21) Appl. No.: 14/908,245

(22) PCT Filed: Aug. 26, 2014

(86) PCT No.: PCT/IL2014/050771
§ 371 (c)(1),
(2) Date: Jan. 28, 2016

(87) PCT Pub. No.: WO2015/029033
PCT Pub. Date: Mar. 5, 2015

(65) Prior Publication Data
US 2016/0175063 A1    Jun. 23, 2016

Related U.S. Application Data

(60) Provisional application No. 61/871,427, filed on Aug. 29, 2013, provisional application No. 61/897,897, filed on Oct. 31, 2013.

(51) Int. Cl.
*A61B 34/00* (2016.01)
*A61B 1/00* (2006.01)
(Continued)

(52) U.S. Cl.
CPC .......... *A61B 34/73* (2016.02); *A61B 1/00006* (2013.01); *A61B 1/00158* (2013.01);
(Continued)

(58) Field of Classification Search
CPC .............. A61B 34/73; A61B 1/100006; A61B 1/00158; A61B 1/0036; A61B 1/041; A61B 5/062
See application file for complete search history.

(56) References Cited

U.S. PATENT DOCUMENTS 3,322,374 A    5/1967  King
3,683,389 A    8/1972  Hollis
(Continued)

FOREIGN PATENT DOCUMENTS

CN    1654027     8/2005
CN    101080198   12/2010
(Continued)

OTHER PUBLICATIONS

Bouchebout et al., "An overview of multiple DoF magetic actuated micro-robots", Journal of Micro-Nano Mechatronics, 2012, pp. 1-19.

(Continued)

*Primary Examiner* — Howie Matthews
(74) *Attorney, Agent, or Firm* — Pearl Cohen Zedek Latzer Baratz LLP

(57) ABSTRACT

An optimization unit controls electrical currents of a set of electromagnets to generate a wanted maneuvering magnetic field pattern (MMP) for moving an in-vivo device in the GI system. The optimization unit may calculate a magnetic force and a magnetic field to maneuver the in-vivo device from a current location and/or orientation to a new location and/or orientation. The optimization unit may solve a magnetic force optimization problem with respect to the magnetic force in order to determine electrical currents suitable for generating the wanted MMP. The optimization unit may additionally or alternatively solve a minimum electrical power optimization problem with respect to the electrical power to be consumed by the electromagnets in order to (Continued)

recalculate or adjust the electrical currents. The optimization unit may solve one or more of the optimization problems while complying with a set of constraints associated with or derived from each type of optimization objective.

21 Claims, 10 Drawing Sheets

(51) Int. Cl.
   *A61B 1/04* (2006.01)
   *A61B 5/06* (2006.01)
(52) U.S. Cl.
   CPC .............. *A61B 1/041* (2013.01); *A61B 5/062* (2013.01); *A61B 1/00036* (2013.01)

(56) References Cited

U.S. PATENT DOCUMENTS

| | | |
|---|---|---|
| 3,893,462 A | 7/1975 | Manning |
| 3,971,362 A | 7/1976 | Pope et al. |
| 4,278,077 A | 7/1981 | Mizumoto |
| 4,429,328 A | 1/1984 | Jones |
| 4,431,005 A | 2/1984 | McCormick |
| 4,651,201 A | 3/1987 | Schoolman |
| 4,656,508 A | 4/1987 | Yokota |
| 4,689,621 A | 8/1987 | Kleinberg |
| 4,741,327 A | 5/1988 | Yabe |
| 4,844,076 A | 7/1989 | Lesho et al. |
| 4,847,617 A | 7/1989 | Silvian |
| 4,944,299 A | 7/1990 | Silvian |
| 5,279,607 A | 1/1994 | Schentag et al. |
| 5,432,543 A | 7/1995 | Hasegawa et al. |
| 5,459,605 A | 10/1995 | Kempf |
| 5,515,853 A | 5/1996 | Smith et al. |
| 5,543,770 A | 8/1996 | Sasaki et al. |
| 5,558,091 A | 9/1996 | Acker et al. |
| 5,604,531 A | 2/1997 | Iddan et al. |
| 5,697,377 A | 12/1997 | Wittkampf |
| 5,764,809 A | 6/1998 | Nomami et al. |
| 5,796,861 A | 8/1998 | Vogt et al. |
| 5,819,736 A | 10/1998 | Avny et al. |
| 5,924,989 A | 7/1999 | Polz |
| 5,946,182 A | 8/1999 | Hertzog et al. |
| 5,993,378 A | 11/1999 | Lemelson |
| 6,120,453 A | 9/2000 | Sharp |
| 6,175,575 B1 | 1/2001 | Ahuja et al. |
| 6,175,757 B1 | 1/2001 | Watkins et al. |
| 6,179,772 B1 | 1/2001 | Blackwell |
| 6,188,355 B1 | 2/2001 | Gilboa |
| 6,233,476 B1 | 5/2001 | Strommer et al. |
| 6,240,312 B1 | 5/2001 | Alfano |
| 6,248,074 B1 | 6/2001 | Ohno et al. |
| 6,324,418 B1 | 11/2001 | Crowley et al. |
| 6,447,448 B1 | 9/2002 | Ishikawa et al. |
| 6,516,213 B1 | 2/2003 | Nevo |
| 6,560,309 B1 | 5/2003 | Becker et al. |
| 6,594,517 B1 | 7/2003 | Nevo |
| 6,632,175 B1 | 10/2003 | Marshall |
| 6,871,086 B2 | 3/2005 | Nevo et al. |
| 6,950,690 B1 | 9/2005 | Meron et al. |
| 7,009,634 B2 | 3/2006 | Iddan et al. |
| 7,118,529 B2 | 10/2006 | Glukhovsky et al. |
| 7,122,001 B2 | 10/2006 | Uchiyama et al. |
| 7,354,398 B2 | 4/2008 | Kanazawa |
| 7,551,955 B2 | 6/2009 | Adler |
| 7,727,169 B1 | 6/2010 | Lewkowicz et al. |
| 8,388,517 B2 | 3/2013 | Yoshizawa |
| 8,428,685 B2 | 4/2013 | Swain |
| 8,450,997 B2 | 5/2013 | Silverman |
| 2001/0017649 A1 | 8/2001 | Yaron |
| 2001/0051766 A1 | 12/2001 | Gazdzinski |
| 2002/0022777 A1 | 2/2002 | Crieghton et al. |
| 2002/0103417 A1 | 8/2002 | Gazdzinksi |
| 2002/0165592 A1 | 11/2002 | Glukhovsky et al. |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0018280 A1 | 1/2003 | Lewkowicz et al. |
| 2003/0028078 A1 | 2/2003 | Glukhovsky |
| 2003/0043263 A1 | 3/2003 | Glukhovsky |
| 2003/0045790 A1 | 3/2003 | Lewkowicz et al. |
| 2003/0077223 A1 | 4/2003 | Glukhovsky et al. |
| 2003/0114742 A1 | 6/2003 | Lewkowicz et al. |
| 2003/0117491 A1 | 6/2003 | Avni et al. |
| 2003/0151661 A1 | 8/2003 | Davidson et al. |
| 2003/0160721 A1 | 8/2003 | Gilboa et al. |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0174208 A1 | 9/2003 | Glukhovsky et al. |
| 2003/0195415 A1 | 10/2003 | Iddan |
| 2003/0216622 A1 | 11/2003 | Meron et al. |
| 2003/0229268 A1 | 12/2003 | Uchiyama et al. |
| 2004/0027459 A1 | 2/2004 | Segawa et al. |
| 2004/0027500 A1 | 2/2004 | Davidson et al. |
| 2004/0130318 A1 | 7/2004 | Saltsov et al. |
| 2004/0138552 A1 | 7/2004 | Harel et al. |
| 2004/0236181 A1 | 11/2004 | Honda et al. |
| 2005/0062562 A1 | 3/2005 | Ries |
| 2005/0064815 A1 | 3/2005 | Kanazawa |
| 2005/0093544 A1 | 5/2005 | Ries |
| 2005/0171427 A1 | 8/2005 | Nevo et al. |
| 2005/0261566 A1 | 11/2005 | Hanley |
| 2006/0063974 A1 | 3/2006 | Uchiyama et al. |
| 2007/0055125 A1 | 3/2007 | Anderson et al. |
| 2007/0191671 A1 | 8/2007 | Kawano et al. |
| 2007/0221233 A1 | 9/2007 | Kawano |
| 2007/0244388 A1 | 10/2007 | Sato et al. |
| 2009/0010571 A1 | 1/2009 | Seki |
| 2009/0048484 A1 | 2/2009 | Swain et al. |
| 2009/0318761 A1 | 12/2009 | Rabinovitz |
| 2010/0010305 A1 | 1/2010 | Kawano |
| 2010/0234685 A1 | 9/2010 | Juloski et al. |
| 2011/0046443 A1 | 2/2011 | Kawano et al. |
| 2011/0054254 A1 | 3/2011 | Reinschke |
| 2011/0301497 A1 | 12/2011 | Shachar et al. |
| 2012/0097870 A1 | 4/2012 | Leray et al. |
| 2012/0108883 A1 | 5/2012 | Peterchev |
| 2012/0149981 A1 | 6/2012 | Khait et al. |
| 2012/0271104 A1 | 10/2012 | Khait |
| 2012/0277529 A1 | 11/2012 | Popescu |
| 2013/0018225 A1 | 1/2013 | Segawa et al. |
| 2013/0053910 A1 | 2/2013 | Hareland |
| 2013/0331649 A1 | 12/2013 | Khait et al. |
| 2014/0003418 A1 | 1/2014 | Khait et al. |
| 2016/0022123 A1 | 1/2016 | Katznelson |

FOREIGN PATENT DOCUMENTS

| | | |
|---|---|---|
| DE | 3440177 | 5/1986 |
| EP | 0894473 | 11/2003 |
| EP | 2119392 | 11/2009 |
| JP | 57-45833 | 3/1982 |
| JP | 3-289773 | 12/1991 |
| JP | 4-109927 | 4/1992 |
| JP | 4-180736 | 6/1992 |
| JP | 5015515 | 1/1993 |
| JP | 6114064 | 4/1994 |
| JP | 6285044 | 10/1994 |
| JP | 7289504 | 11/1995 |
| JP | 2000-023980 | 5/2000 |
| JP | 2001-046358 | 2/2001 |
| JP | 2001137182 | 5/2001 |
| JP | 2001224551 | 8/2001 |
| JP | 2001224553 | 8/2001 |
| JP | 4109927 | 3/2004 |
| JP | 2012-232126 | 11/2012 |
| WO | WO 92/21307 | 12/1992 |
| WO | WO 98/11816 | 3/1998 |
| WO | WO 2000/010456 | 3/2000 |
| WO | WO 2001/006917 | 2/2001 |
| WO | WO 2001/008548 | 2/2001 |

(56) References Cited

FOREIGN PATENT DOCUMENTS

| WO | WO 2004/028336 | 4/2001 |
|---|---|---|
| WO | WO 2001/050941 | 7/2001 |
| WO | WO 2001/065995 | 9/2001 |
| WO | WO 2001/065995 | 7/2002 |
| WO | WO 2002/067593 | 8/2002 |
| WO | WO 2003/021529 | 3/2003 |
| WO | WO 2004/036803 | 4/2004 |
| WO | WO 2004088488 | 10/2004 |
| WO | WO 2008/018076 | 2/2008 |
| WO | WO 2008/026549 | 3/2008 |
| WO | WO 2009/087601 | 7/2009 |
| WO | WO 2011/072060 | 6/2011 |
| WO | WO 2012/150596 | 11/2012 |
| WO | WO/2014/141251 | 9/2014 |
| WO | WO 2014/141285 | 9/2014 |
| WO | WO 2012/127469 | 9/2015 |

OTHER PUBLICATIONS

Toennies et al., "Swallowable medical devices for diagnosis and surgery: the state of the art" Vanderbilt University, Dec. 9, 2009, pp. 1397-1414.

BBC News Online—"Pill camera to 'broadcast from the gut'", Feb. 21, 2000, www.news.bbc.co.uk.

Machine Vision: Theory, Algorithms, Practicalities—E.R. Davies, Academic Press 1996, pp. 441-444.

Weitschies, et al., "Magnetic marker monitoring of disintegrating capsules", European Journal of Pharmaceutical Sciences 13 (2001), pp. 411-416.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

Video Camera to "TAKE"—RF System lab, Dec. 25, 2001.

www.rfnorkia.com—NORIKA3, Dec. 24, 2001.

Robots for the future—Shin-ichi, et al., Nov. 29, 2001.

"The Radio Pill", Rowlands, et al., British Communications and Electronics, Aug. 1960, pp. 598-601.

"Wellesley company sends body montiors into space"—Crum, Apr. 1998.

"Wireless transmission of a color television moving image from the stomach using a miniature CCD camera, light source and microwave transmitter". Swain CP, Gong F, Mills TN. Gastrointest Endosc 1997;45:AB40.

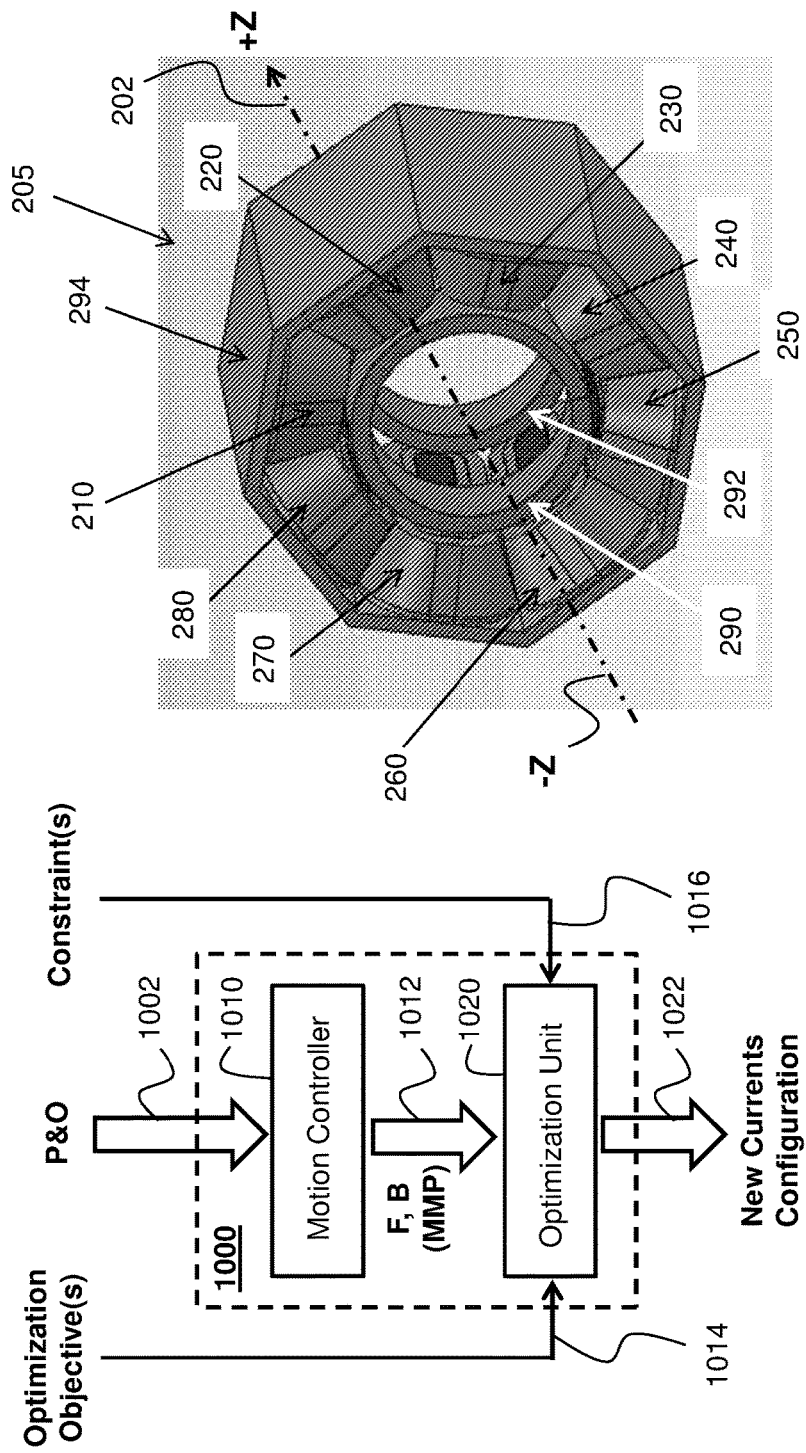

SYSTEM AND METHOD FOR MANEUVERING COILS POWER OPTIMIZATION

CROSS-REFERENCE TO RELATED APPLICATIONS

This application is a National Phase Application of PCT International Application No. PCT/IL2014/050771, entitled "SYSTEM AND METHOD FOR MANEUVERING COILS POWER OPTIMIZATION", International Filing Date Aug. 26, 2014, published on Mar. 5, 2015 as WO 2015/029033, which in turn claims priority from U.S. Patent Application No. 61/871,427, filed Aug. 29, 2014, and U.S. Patent Application No. 61/897,897, filed Oct. 31, 2013, all of which are incorporated herein by reference in their entirety.

FIELD OF THE INVENTION

The present invention generally relates to maneuvering of a magnet in a magnetic field and more specifically to a magnetic field based maneuvering system and methods for maneuvering a swallowable in-vivo device, and to optimization methods based on which an electrical power is provided to the maneuvering system.

BACKGROUND

In-vivo measuring systems and other types of in-vivo systems (e.g., in-vivo devices for performing surgical and the like operations) are known in the art. Some in-vivo devices/systems, which may traverse the gastrointestinal ("GI") system (mouth-to-anus), or other body organs/systems, may include an imaging sensor, or imager, for imaging (e.g., capturing images of) the interior of the GI system. An in-vivo device may include one or more imagers. Other in-vivo devices may alternatively or additionally include a medication container and means for administering medication in the GI system. Other in-vivo devices may include means for performing surgical operations in vivo, and so on. Autonomous in-vivo devices are devices that traverse the GI system by being pushed through the GI system by peristaltic force exerted by the digestive system. Autonomous in-vivo devices may also spasmodically move in the intestinal tract in 'fits and starts'.

Moving a device in vivo by using a peristaltic force has drawbacks. For example, the in-vivo device may get uncontrollably stuck somewhere in the GI system for an unknown period of time; the device may capture images in one direction while a nearby area, which may be clinically more interesting, is not imaged sufficiently or at all, etc.

There exist magnetic maneuvering systems for maneuvering in-vivo devices magnetically. A device may be maneuvered magnetically by incorporating a magnet in it. Such maneuvering systems may be designed to magnetically move an in-vivo sensing device from one spatial location to another, and change its spatial orientation (e.g., roll angle, pitch angle and/or yaw angle).

Conventional magnetic maneuvering systems have drawbacks. For example, some systems are allowed to be overly robust in order to be able to provide large magnetic-field generating electrical currents while permitting the maneuvering systems to consume excessive electrical power. Conventional magnetic maneuvering systems are indiscriminative with respect to optimization of the magnetic field and force output to various regions of the GI system.

For example, assuming that a magnetic maneuvering system can generate a maneuvering magnetic field pattern ("MMP") for maneuvering a device by using various sets of electrical currents, where each current is provided to an electromagnet, it would be beneficial to be able to select the set of electrical currents such that generating the MMP by these currents would result in a magnetic force that is as close to a desired magnetic force as possible, and, if required, in a total electrical power that is as minimal as possible.

SUMMARY

An optimization unit may control electrical currents of maneuvering electromagnets in order to generate a maneuvering magnetic field pattern (MMP) that can move an in-vivo device in the GI system. A controller (e.g., a motion controller) may calculate a value of a desired magnetic force and/or a desired magnetic field that may depend, for example, on the location/orientation (current or intended/target) of the device in the GI system and, optionally, on the device's speed/velocity in the GI system. The controller may output (and transfer; e.g., to an optimization unit) data that may represent, for example, a first set of magnetic field particulars or data consisting of, or representing, a first magnetic field, a first magnetic force and a first magnetic torque for moving the in-vivo device. The optimization unit may receive the data representing the first set of magnetic field particulars, and it may select, as an optimization objective, a wanted magnetic force or wanted magnetic field (for example the magnetic force/field calculated by the controller or a magnetic field derived from or otherwise associated with it). The optimization unit may solve the optimization objective to find an optimal configuration or set of electrical currents to or for the electromagnets such that providing these electrical currents to the maneuvering electromagnets results in a magnetic force that is as close to the desired magnetic force as possible. The optimization unit may find the optimal set of electrical currents such that a set of predetermined or preselected constraints associated with, or derived from, the optimization objective would be complied with.

The optimization unit may additionally or alternatively select, as an optimization objective, a minimal electrical power (the power consumed by the electromagnets). The optimization unit may solve the minimum power optimization objective to find an optimal configuration or set of electrical currents for the electromagnets such that the resulting total electrical power consumed by the electromagnets to which these currents are provided, would be minimal. The optimization unit may find the optimal set of electrical currents such that a set of predetermined constraints associated with, or derived from, the minimal electrical power optimization objective would be complied with. The wanted magnetic force and the set of constraints to be used with any optimization objective may depend on, or set according to, the current location and/or orientation and/or speed/velocity of the maneuvered device in the GI system/tract.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 1A shows a high-level block diagram of an electrical power optimization system according to an example embodiment;

FIG. 2 depicts a maneuvering electromagnets system according to an example embodiment;

DETAILED DESCRIPTION

Figure 1:
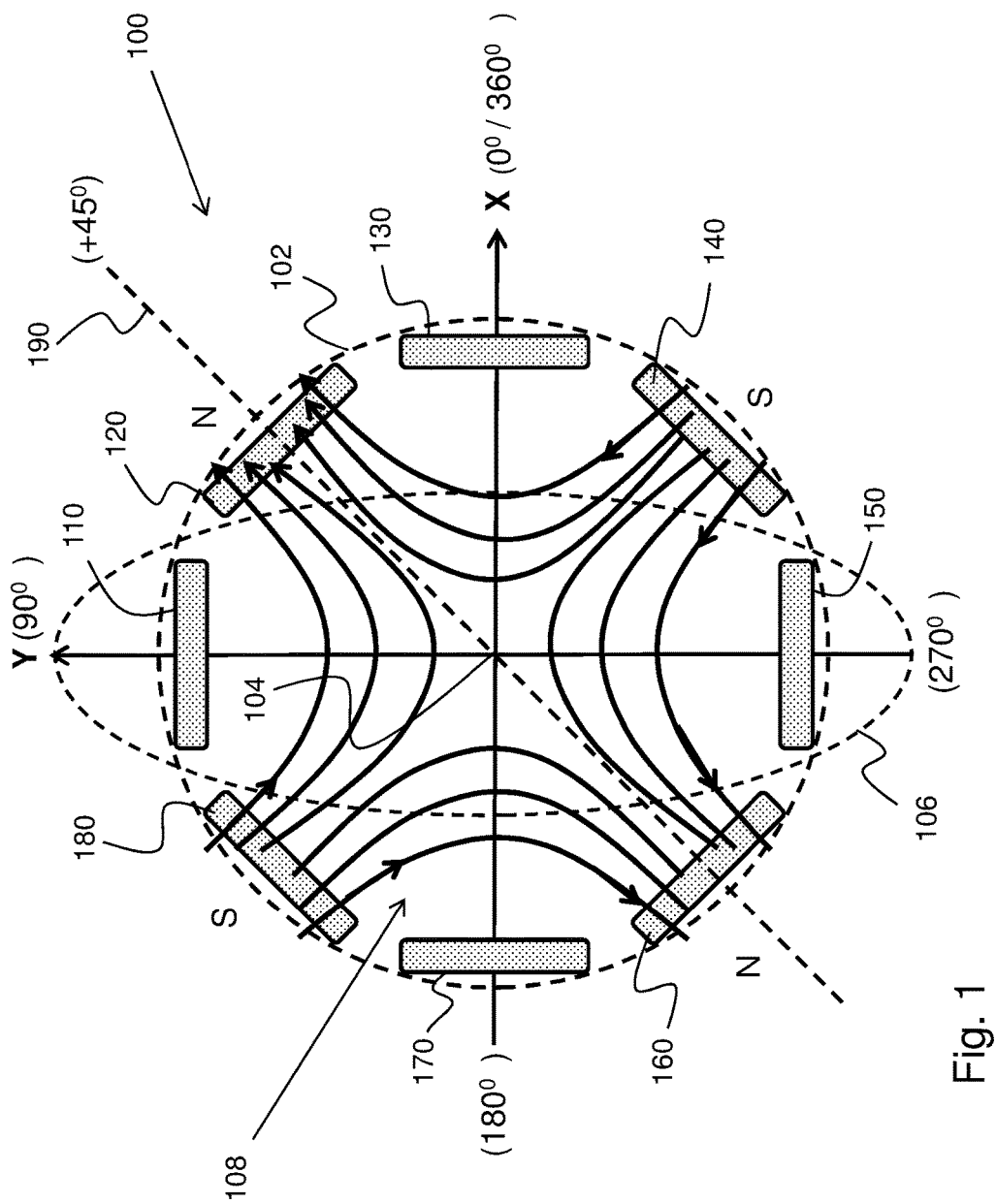
FIG. 1 illustrates a circular electromagnets assembly/setup according to an example embodiment.

The description that follows provides various details of exemplary embodiments. However, this description is not intended to limit the scope of the claims but instead to explain various principles of the invention and the manner of practicing it.

A magnetic maneuvering system may include, for example, a motion controller for controlling movement of an in-vivo device in a desired direction and/or desired velocity, and an optimization unit for selecting or calculating an optimal set of electrical currents for a set of electromagnets in compliance with an optimization objective subjected to a related set of constraints. Calculating electrical currents of electromagnets involves solving a system of partial differential equations, and solving the equations requires using some constraints. The optimization unit may output a solution (e.g., in the form of a set of electrical currents, or currents configuration, or data representing such currents, to or for the electromagnets), for example while using a linear system of equations.

Assuming that an electromagnet is coreless (it includes no 'magnetic' core), a magnetic field (B) generated by such electromagnet linearly depends on the electrical current that passes through/in the electromagnet. Since magnetic force (F) and magnetic torque (T) linearly depend on the magnetic field that produces them, the magnetic force and magnetic torque linearly depend on the electrical current as well. Because of the linear relationship between electrical current and magnetic field B, magnetic force F and magnetic torque T, it is beneficial (e.g., for simplicity reasons), in a magnetic maneuvering system, to calculate electrical currents for the maneuvering electromagnets by solving a set of linear equations. However, since the maneuvering electromagnets may include an iron core, the 'linear' electrical currents are compensated for the de-linearization effect caused by the cores. (By 'linear electrical current' is meant an electromagnet's current sustaining a linear relationship between the electrical current and the magnetic field/force/torque; e.g., in the absence of a magnetic core. By 'actual current' is meant herein a version of the linear current that factors in, or is compensated for, non-linearity due to the electromagnets' core.) Therefore, while electromagnets of the present invention are driven by (fed with) 'actual currents', recalculation of the electromagnets' currents (e.g., scaling currents down, or decreasing them proportionally) is performed in the linearity domain/space. That is, if required, the actual currents can iteratively be converted back to linear currents, recalculated (e.g., scaled down by using a scale down factor), and the resulting current values may be converted back to (different or new) actual currents.

Some embodiments are described below as including, or using, eight electromagnets. However, other numbers of electromagnets may be used; e.g., less than eight electromagnets (e.g., four electromagnets, etc.), or more than eight electromagnet (e.g., nine electromagnets, ten electromagnets, etc.)

FIG. 1 illustrates circularly positioned electromagnets system 100 according to an example embodiment of the invention. In general, N electromagnets may be positioned circularly and form a plane (e.g., X-Y plane, as demonstrated by FIG. 1), for example, such that each electromagnet may have a paired, conjugated, electromagnet on the opposite side of the circle. By way of example, N=8, that is, electromagnets system 100 may include eight electromagnets (designated as 110, 120, 130, 140, 150, 160, 170 and 180), which form, or are circularly circumscribed by, a circle 102. Circular electromagnets system 100 may form, or lie on, a plane coinciding with the Cartesian X-Y plane having a normal in the direction of the Z axis.

Electromagnets 110 through 180 may functionally be divided into four pairs of conjugated electromagnets, where each pair may include a first electromagnet and a second electromagnet that may be positioned opposite the first electromagnet. The electromagnets of electromagnets system 100 may equidistantly be distanced from the coordinate's origin 104 and equidistantly spaced apart on circle 102, with the same angle separating any two adjacent electromagnets.

One example pair of electromagnets (the pair is shown at 106) may include two electromagnets, designated as 110 and 150, on the Y axis; two electromagnets, designated as 120 and 160, in a direction 190 that may be at an angle of +45 degrees with respect to the Y axis; two electromagnets, designated as 130 and 170, on the X axis; and two electromagnets, designated as 140 and 180, in a direction that may be at an angle of (−45) degrees with respect to the X axis.

A wanted/required magnetic maneuvering pattern (MMP) (e.g., magnetic fields and magnetic gradients for maneuvering a device) may be generated by using more than one combination of electromagnets, including more than one combination of current magnitudes and current directions. As explained herein, a MMP may include a magnetic field whose direction may be in any desired direction, including only in the X axis/direction, or only in the Y axis/direction, or only in the Z axis/direction, or in any intermediate/intervenient direction (e.g., at any angle with respect to any axis). An example MMP is shown at 108. Example EMP 108 has magnetic field whose direction(s) is(are) in the X-Y plane but not in the Z direction. (Other MMPs may have magnetic field in other directions in the X-Y plane, and also in the Z direction, as explained herein, provided that the coils system includes electromagnets positioned such that they can generate magnetic fields in the Z direction.) The orientation of MMP 108 may controllably be changed to a different orientation, for example, by shutting down (switching off the currents passing through) electromagnets 120, 140, 160 and 180, and using a different set of electromagnets, for example electromagnets 110, 130, 150 and 170. Orientation when referred to herein may mean the direction the device points or the angular position or attitude of the device, or a representation of the placement of the object in a rotational coordinate system. Such electromagnets swapping may result, for example, in a rotation of the MMP by 45 degrees counterclockwise or 45 degrees clockwise, depending on the direction of the electrical currents of the various electromagnets.

The magnetic field generation scheme shown in FIG. 1 provides for enhanced/improved maneuverability, for example, of in-vivo devices, because it enables generating a magnetic field in any spatial direction within a three-dimensional operating region, and, in addition, it provides for independent control of the direction of the magnetic field, which aligns a device, and the direction and magnitude of the magnetic gradient, which sets the direction and magnitude of the force applied to the maneuvered device.

FIG. 1A shows a block diagram of an optimization system 1000 according to an example embodiment. Optimization system 1000 may include a motion controller 1010, as an example controller, and an optimization unit 1020. Motion controller 1010 may receive location and/or orientation (P&O) data (1002). P&O data 1002 may include data representing or regarding the current location and orientation (current P&O) of a magnetically maneuverable device (e.g., an in-vivo device including a magnet) and data representing or regarding the next (e.g., new) P&O of the device. To the P&O data 1002 may be annexed data representative of a speed with which the in-vivo device should be move to the next or new P&O. Motion controller 1010 may use P&O data 1002 to calculate a first set of magnetic data or particulars: e.g., a (first) magnetic force ($\vec{F}$) required to move the device and/or a (first) magnetic field $\vec{B}$ and/or (first) torque ($\vec{T}$) that is/are required to change its orientation. Motion controller 1010 may, then, output data (1012) representing the calculated (first) set of magnetic field data or particulars, for example a first/calculated magnetic force, $\vec{F}$, and a first/calculated magnetic field, $\vec{B}$, to optimization unit 1020. ($\vec{F}$ and $\vec{B}$, which motion controller 1010 calculates for moving and orienting the device, make, form, create or have an associated maneuvering magnetic field pattern (MMP). Data 1012 may, thus, represent a wanted/desired MMP for maneuvering the device.) A value of a magnetic force may depend on, or be a function of, a factor selected from a group of factors consisting of: a location of the device in the gastrointestinal system and the speed/velocity of the device in the gastrointestinal system.

Units such as controller 340, optimization system 1000, motion controller 1010, optimization unit 1020, controller 460, and other processors or processing units described herein may be or include, or may be included within, one or more processors or controllers, which may be for example a dedicated processor or controller or a general purpose processor or controller configured to carry out embodiments of the present invention by for example executing software or code.

Optimization unit 1020 may receive data 1012 from motion controller 1010 in order to use the data to optimize a set of electrical currents (e.g., to find a 'current solution') and to provide the optimized set of currents to maneuvering electromagnets to generate wanted or desired magnetic field particulars to controllably maneuver the in-vivo device. In addition, optimization unit 1020 may receive data 1014 that may represent one or more optimization objectives, and data 1016 that may represent a set of constraints for, associated with or derived from each optimization objective. Using constraints enables optimization unit 1020 to find an electrical current solution for the maneuvering system that is optimal in terms of selection of the electrical currents of the electromagnets, magnetic field/force/torque, electrical power consumed by the maneuvering system, etc.

Assuming that a magnetic maneuvering system includes N electromagnets, optimization unit 1020 may control the electrical currents provided to the N electromagnets to thereby generate a maneuvering magnetic field pattern within an operating region (e.g., within a particular region of the GI tract) to controllably move an in-vivo device within that region. Optimization unit 1020 may receive data, for example from motion controller 1010, that may represent the first (calculated) set of magnetic field data or particulars (1012) consisting, for example, of a first magnetic field (B), a first magnetic force (F) and, optionally, a first magnetic torque (T) for moving the in-vivo device. The first set of magnetic field particulars may be calculated by the motion controller according to data representing location and/or orientation (P&O; at 1002) of the in-vivo device in the digestive/gastrointestinal tract of a subject.

Optimization unit 1020 may select, based on P&O data, one or more optimization objectives from the group consisting of (i) a minimum difference between a value of a second (output) magnetic field particular, which is to be actually applied to the in-vivo device in a predetermined direction, and a value of the first magnetic field particular calculated by motion controller 1010, and (ii) a minimum value for the electrical power ($P_{min}$) to be consumed by the electromagnets generating the MMP. (A second magnetic field particular may be a second magnetic field, a second magnetic force, or a second magnetic torque.) Optimization unit 1020 may also select a set of constraints that may be associated with, or derived from, the selected optimization objective(s) and with the first (calculated) set of magnetic field data or particulars. (The set of constraints may be selected depending on the used optimization objective and the first (calculated) magnetic field particulars.)

Optimization unit 1020 may output (1022) and provide an optimal set of electrical currents to maneuvering electromagnets such that the magnetic field particulars jointly generated by the electromagnets satisfy the selected optimization objective(s), and the selected set(s) of constraints respectively associated with, or derived from, the selected optimization objective(s) are complied with.

Optimization unit 1020 may select a set of one or more constraints from a group consisting of: (a) a permissible value, or range, of the magnetic field (B), (b) a permissible value, or range, of the magnetic force (F), (c) a permissible value, or range, of the magnetic torque (T), (d) a permissible value, or range, of a direction ($\alpha$) of the magnetic field, (e) a permissible value, or range, of a direction ($\beta$) of the magnetic force, and (f) a permissible value, or range, of a ratio (R) between the magnetic field (B) and the magnetic force (F) (R=B/F). (Other or additional types of constraints may be used.)

Optimization unit 1020 may select the second magnetic force ($\vec{F}$) based on (i) the current location and/or current orientation of the in-vivo device, or (ii) the new location and/or new orientation of the in-vivo device, or (iii) both the current and new location and/or orientation of the in-vivo device. The second magnetic force, which may be regarded as an actual or wanted magnetic force, may be identical to the first magnetic force, which may be regarded as an initial or target magnetic force. The second magnetic force may differ from the first magnetic force. For example, the second magnetic force may be weaker than the first magnetic force. The second magnetic force may be selected from a group consisting of: (i) a maximum magnetic force (Fmax) that can be generated, for example, by using selected electrical currents or selectively manipulated currents, and (ii) a magnetic force which is less than the maximum magnetic force.

Optimization unit 1020 may solve a magnetic force optimization problem for the second magnetic force in order to obtain a first set of electrical currents to potentially drive the electromagnets. Optimization unit 1020 may additionally or alternatively solve a "minimum electrical power" optimization problem to obtain a second set of electrical currents to potentially drive the electromagnets. Optimization unit 1020 may decide to solve, or to refrain from solving, the "minimum electrical power" optimization problem depending on various factors, for example, depending on: (i) a region of the digestive (gastrointestinal) tract the in-vivo device is at or in, and/or the device's speed/velocity, or (ii) the magnitude of the magnetic force required to move the in-vivo device. (Optimization unit 1020 may use other decision criteria.) Optimization unit 1020 may provide to the electromagnets the first set of electrical currents when/if no "minimum electrical power" optimization problem is to be solved, and may provide the second set of electrical currents to the electromagnets when/if the "minimum electrical power" optimization problem is solved.

After optimization unit 1020 solves the optimization problem, or problems, to find the best, or more suitable, set of electrical currents that complies with the optimization objective(s) and associated or derived constraints, optimization unit 1020 outputs data or signal (1022), which represents the optimal solution of the electrical currents (e.g., the optimization solution), to a controller (e.g., a current controller, not shown in FIG. 1A) that may use data/signal 1022 to modify or adjust the currents of the electromagnets accordingly, to thereby generate magnetic field particulars that are as close to the wanted ones as possible, and that comply with the associated or derived set of constraints.

FIG. 2 depicts a maneuvering electromagnets setup 205 that includes an electromagnets system similar to circular electromagnets system 100 of FIG. 1 and, in addition, 'Z' coils/electromagnets (implemented as Helmholtz pair of circular coils) according to an example embodiment of the invention. A 'Z-coil' is a coil/electromagnet that may lie on, or coincide with, the X-Y plane (or lying on a plane parallel to the X-Y plane), which is perpendicular to the Z axis (202). (A Z-coil may form a plane having a normal in the Z direction.) A Z-coil may generate a magnetic field, and a magnetic field gradient, in the Z direction (e.g., in the +Z direction or in the −Z direction). FIG. 2 depicts two Z-coils, designated as 290 and 292. Additional Z-coils may be interposed in-between Z-coils 290 and 292 to enhance the magnetic field in the Z direction, for example to make the magnetic field in the Z more uniform and, if required, stronger. Coils/electromagnet 210 through 280 and Z-coils 290 and 292 are shown encapsulated by a shell/housing that may be octagon, as shown at 294.

Figure 3A:
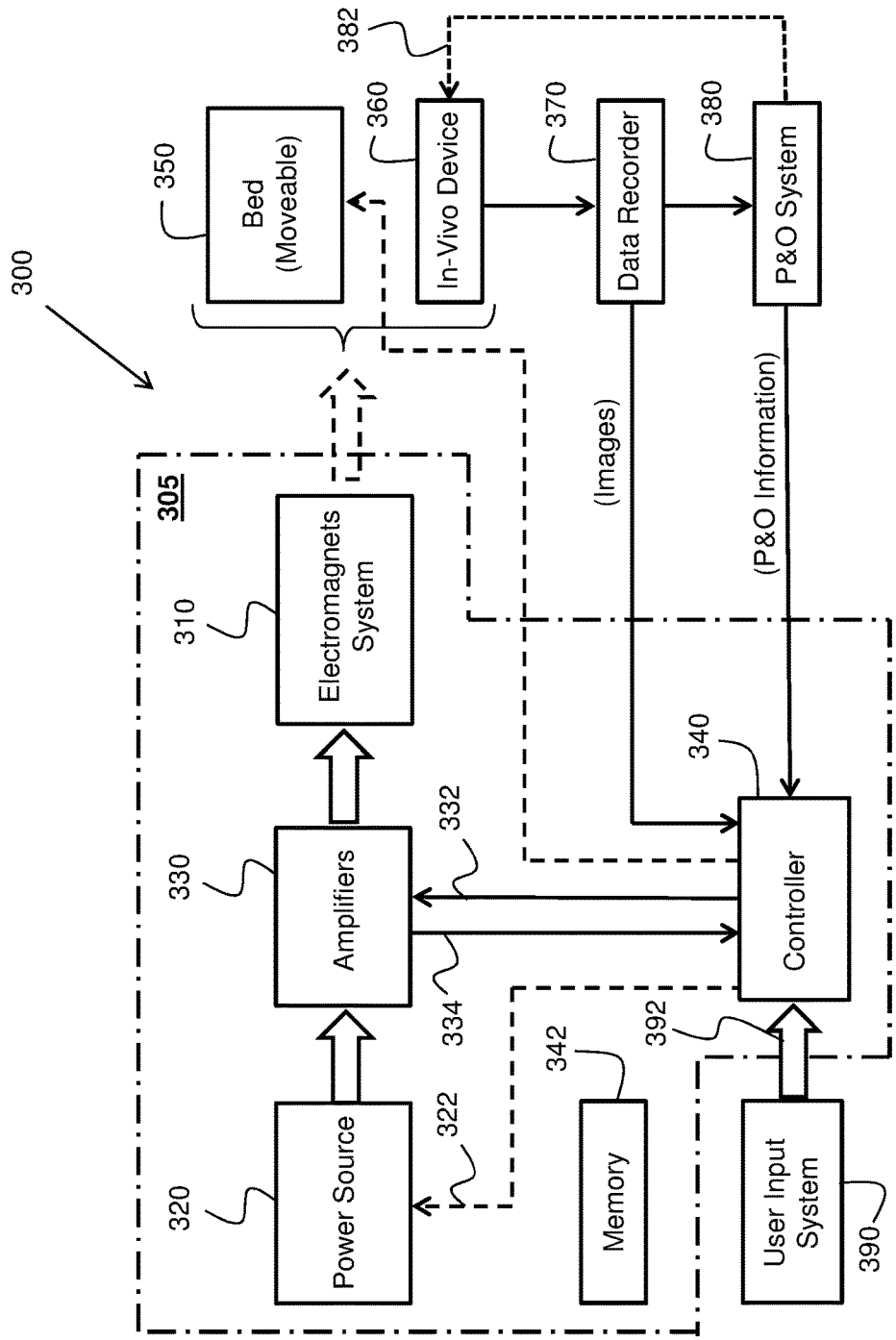
FIG. 3A is a block diagram of a magnetic maneuvering system according to an example embodiment.

FIG. 3A is a block diagram of a magnetic maneuvering system 300 according to an example embodiment of the invention. Magnetic maneuvering system 300 may include a magnetic maneuvering control system 305, a bed 350 on which a subject may lie, a data recorder/receiver 370, and position and orientation (P&O) system 380. An in-vivo device 360 may be swallowed by the subject before or while the subject lies on bed 350. Bed 350 may be controllably moveable.

Magnetic maneuvering control system 305 may include a maneuvering coils/electromagnets system 310, which may be identical or similar to maneuvering coils/electromagnets system 205 of FIG. 2, a power source 320 that may be configured to provide electrical currents to the coils/electromagnets of coils/electromagnets system 310, amplifiers 330 (e.g., an amplifier per coil/electromagnet) for individually adjusting the electrical current (including value and direction) of each coil/electromagnet of coils/electromagnets system 310, a controller 340 for controlling a MMP, for example, by changing the electrical state of the amplifiers by individually controlling an electrical parameter (e.g., amplification/gain, conduction, etc.) of each amplifier, and a memory 342. Controller 340 may, based on P&O information it receives from P&O system 380, control movement of in-vivo device 360 by using/operating amplifiers 330 and electromagnets system 310 to generate a wanted magnetic field gradient in a wanted direction in order to move in-vivo device in a desired direction and in a desired speed. Electromagnet system 310 may include N electromagnets, and amplifiers unit 330 may be controlled by controller 340 to output, and to respectively provide, a set of N electrical currents to the N electromagnets. Memory 342 may store an instruction code (e.g., for controller 340), P&O information/data, user input data, etc.

A subject having ingested in-vivo device 360 may lie on bed 350. In-vivo device 360 may wirelessly transmit image data pertaining to images acquired in the subject's GI system, and possibly data of other type(s), to data recorder/receiver 370. (Recorder/receiver 370 may be incorporated into or attached to a gantry containing coils 310.) Recorder/receiver 370 may transfer image data, and possibly other types of data (e.g., location and/or orientation data), to controller 340. Controller 340 may display transferred images to a display device, and may use them, or any other information, for example, to navigate or maneuver in-vivo device 360 in the subject's GI system.

P&O system 380 may transmit localization signals (382) in proximity to the subject's GI system, and a localization signal sensor (e.g., sensing coil(s)) residing in in-vivo device 360 may sense the localization signals and transmit raw, pre-processed or fully processed P&O data, which are related to the in-vivo device's current P&O, to data recorder 370. Data recorder 370 may transfer the P&O data pertaining to the current device's P&O to P&O system 380. Depending on the processing capability of data recorder 370, P&O system 380 may process, or further process, or fully analyze the P&O data and transfer corresponding P&O information to controller 340.

A user (e.g., a physician) may use an input system 390 to transfer P&O data to controller 340 regarding a wanted P&O or a next or intended P&O of in-vivo device 360. Controller 340 may analyze the wanted/next/intended P&O relative to the current P&O information and, based on the difference, controller 340 may determine (e.g., by calculation) the magnitude and/or direction of the magnetic field and magnetic force that should be generated in order to move in-vivo device 360 from the current P&O to the wanted/next P&O. Controller 340 may, then, calculate the electrical currents to be provided to electromagnets 310 in order to generate the magnetic field and magnetic force according to the determined magnitude and/or direction. Then, controller 340 may output/transfer (332) a corresponding signal, or signals, to amplifiers 330 to accordingly adjust an electrical parameter of one or more of amplifiers 330. The adjusted electrical currents, then, may be fed or provided to electromagnets 310 to maneuver in-vivo device 360 to the next, intended, or new P&O. Controller 340 may monitor (334), for example it may get feedback regarding, the state of amplifiers 330, and use the feedback information in conjunction with the P&O data/information to control the state of amplifiers 330. Controller 340 may also control (322) power source 320, for example, to change the electrical currents' dynamic range. That is, controller 340 may control the various electrical currents coarsely by controlling the electrical state of power source 320, and the electrical currents may be fine-tuned by controller 340 by using amplifiers 330.

Controller 340 may be configured to operate N electromagnets to simultaneously generate or produce a magnetic field that aligns an in-vivo device in a first direction, and a magnetic gradient to exert/apply force on the in-vivo device in a second direction, to thereby manipulate (controllably change) the location and/or orientation of the in-vivo device. The direction of the magnetic gradient (the second direction) may be, for example, parallel to the first direction (the direction of the magnetic field), or at an angle with respect to the first direction. Controller 340 may selectively activate one or more electromagnets in order to generate a wanted or required MMP. That is, not all electromagnets of electromagnets system 310 have to be activated or used in order to generate a particular MMP. Controller 340 may receive (e.g., from P&O system 380) a P&O data representative of a current P&O of in-vivo device 360, for example, in the GI system of a subject positioned in the circularly positioned N electromagnets, and it may obtain (392), for example from a user/operator, data representative of an intended P&O of the in-vivo device in the GI system. Controller 340 may, then, generate and forward a control signal (332) to amplifiers 330 to thereby control the electrical currents (magnitudes and directions) for the N electromagnets based on the P&O data.

Figure 3B:
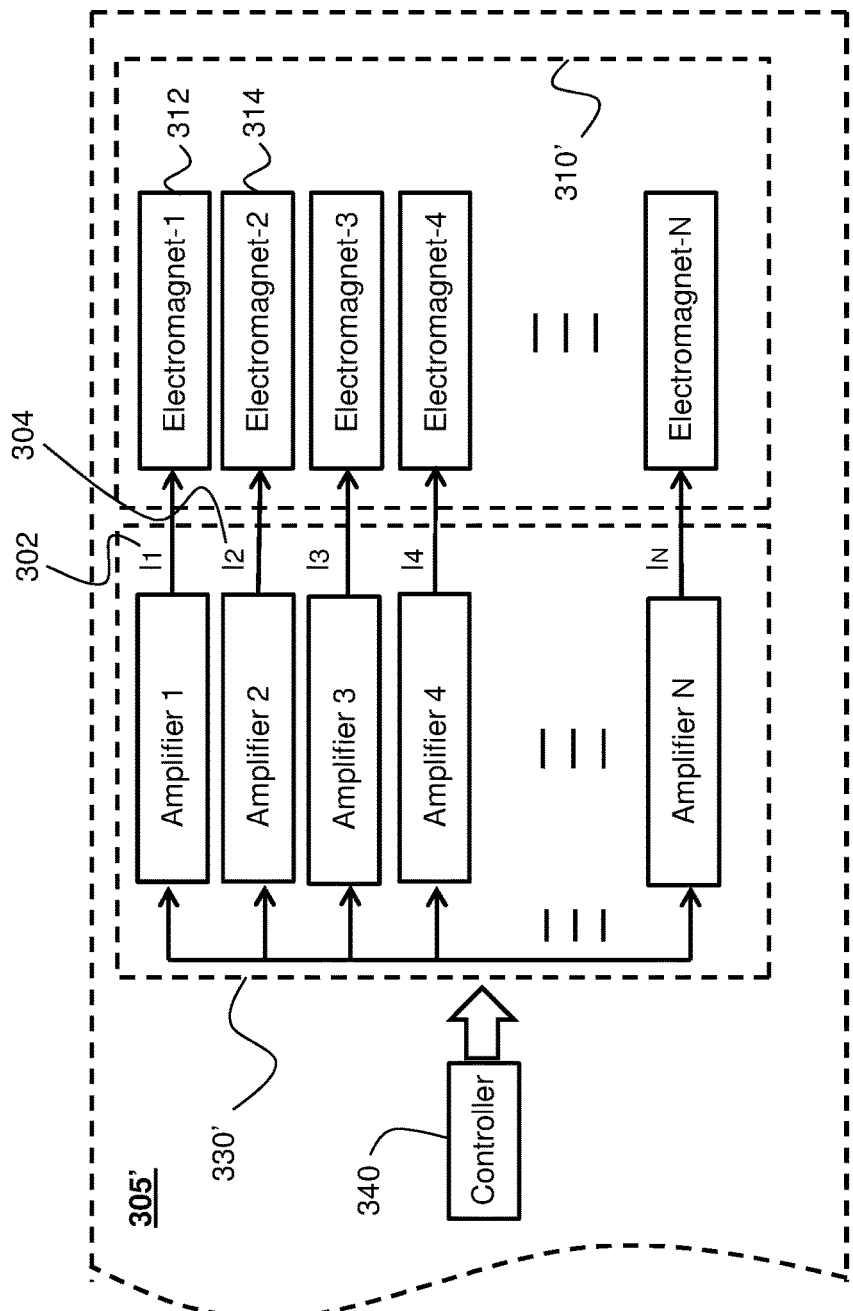
FIG. 3B is a block diagram of a magnetic maneuvering control system according to an example embodiment.

FIG. 3B is a partial block diagram of a magnetic maneuvering control system 305' according to an example embodiment of the invention. Magnetic maneuvering control system 305' may include an electromagnetic system 310' that may include N electromagnets, designated as Electromagnet-1 (shown at 312), Electromagnet-2 (shown at 314), . . . , Electromagnet-N. The N electromagnets (e.g., N=8) may function in the way described herein. Magnetic maneuvering control system 305' may also include N amplifiers, shown at 330', for example one amplifier per electromagnet. The N amplifiers may respectively supply N electrical currents to the N electromagnets. For example, amplifier 'Amplifier 1' may supply electrical current I1, shown at 302, to Electromagnet-1, amplifier 'Amplifier 2' may supply electrical current I2, shown at 304, to Electromagnet-2, and so on. (Other amplifier configurations may be used. For example, an amplifier having multiple electrical current outputs may be used.)

An in-vivo device (e.g., in-vivo device 360) may be forced to move from one location to another, or forced to change its orientation, by using more than one current solution. (The term 'current solution' refers to a selected set of electromagnets and electromagnet currents that jointly generate a magnetic maneuvering pattern (MMP) required to maneuver an in-vivo device to a wanted or required location or orientation.) Namely, a same (or resembling) MMP may be generated by using different electrical current solutions, where different electrical current solutions may refer (e.g., include usage of) different sets of electromagnet currents $I_1$ (shown at 302), $I_2$ (shown at 304), $I_3$, . . . , $I_N$. (Selection of an electromagnet's current Ii means selection of the value of the electromagnet's current and direction (e.g., negative direction or positive direction). Selecting an electrical current also means selection of the pertinent electromagnet.) However, the overall electrical power consumed/drawn by the system's power source (e.g., power source 320 of FIG. 3A) and peripherals (e.g., electromagnets, control system, etc.) in order to drive the system's electromagnets may vary between sets of electromagnets and currents. That is, a selection of a particular set of electromagnets and electromagnet currents may be more economical (in terms of total electrical power) than other sets, which calls for an optimization process with respect to which set of electromagnet currents better suits a particular maneuvering requirement or MMP in terms of; e.g., total electrical power. Controller 340 may, in selecting electromagnets and electromagnets' currents, execute an optimization procedure/program to determine which set of electromagnets and electromagnet currents are optimal (e.g., in terms of wanted magnetic force, power consumption, etc.) for any maneuvering requirement (e.g., for generating a MMP for maneuvering a device from one point to another in a three-dimensional operating region, etc.). Controller 340 of FIGS. 3A-3B, by executing software or instructions, may carry out steps which are performed by any of optimization system 1000, motion controller 1010 and optimization unit 1020, and thus may function as these units.

Figure 4:
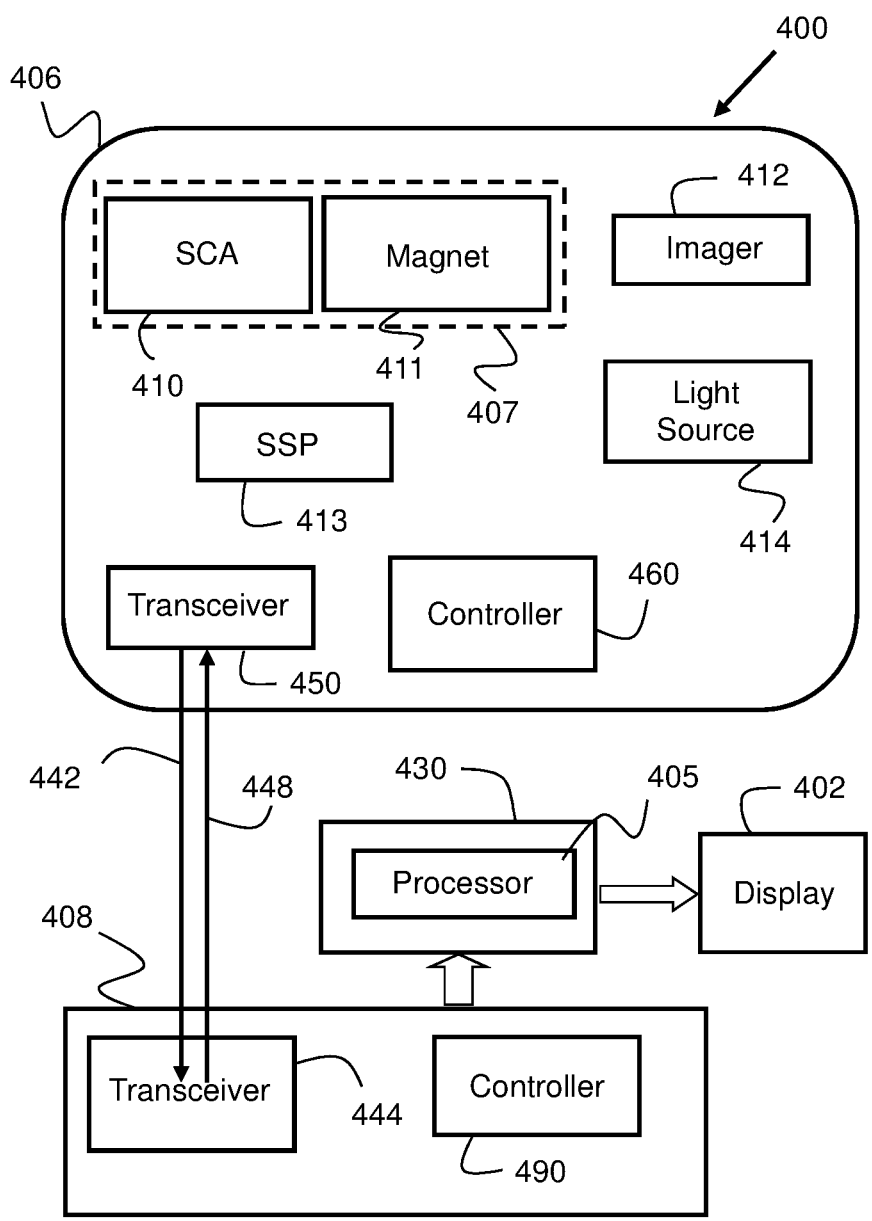
FIG. 4 is a block diagram of an in-vivo system according to an example embodiment.

FIG. 4 shows an in-vivo imaging system 400 according to an example embodiment. In-vivo imaging system 400 may include an in-vivo device 406 with an imager 412, a data recorder 408, a workstation 430, which may be, for example, a workstation or personal computer, and a display device 402 for displaying, for example, images and/or a video clip or moving image stream, and for displaying information related to the location and/or orientation of the in-vivo device, etc. Workstation 430 may functionally be connected to maneuvering system 305 of FIG. 3A, and display (e.g., on display device 402) various data regarding set(s) of electromagnets and electromagnet currents and/or potential electromagnets and potential electromagnet currents that are, or that may be, used to maneuver device 406.

By way of example, in-vivo device 406 may include one imager (e.g., imager 412), or more imagers. In-vivo device 406 may also include a light/illumination source 4914 for illuminating a GI section/site/organ to be imaged, a controller 460, which may execute some or all of steps or procedure(s) executed by controller 340, optimization unit 1020, or other units described herein, a storage unit 440 for storing data, a transceiver 450 for transmitting (442) image frames and, optionally, for receiving (448) data and/or commands from data recorder 408, and an electrical power source for powering the device (406).

In-vivo device 406 may include a location and steering unit (LSU) 407. LSU 407 may include a sensing coil assembly (SCA) 410 for sensing localization signals generated, for example, by an external localization system (not shown). SCA 410 may include k sensing coils for sensing electromagnetic localization fields/signals through electromagnetic induction, where k is an integer equal to or greater than 1 (e.g., k=2, or k=3) that may be, for example, mutually perpendicular. The current location, and optionally the current orientation, of in-vivo device 406 may be determined based on the EMF signal(s) sensed by (induced in) SCA 410.

Device 406 may also include a permanent magnet 411 that may interact with a magnetic field generated, for example, by the magnetic maneuvering system 305 of FIG. 3A, or by a similar system. Magnet 411, in conjunction with a magnetic field, may produce magnetic forces and/or torques to maneuver device 406 in a desired direction or to orient or position it in a desired orientation/direction. Device 406 may include a sensing signal processor ("SSP") 413 for measuring the magnitude of the EMF signals induced in SCA 410. Controller 460 may use transceiver 450 to transfer data that represents the EMF signals (P&O data of device 406) to data recorder 408.

Data recorder 408 may include, for example, a transceiver 444 and a controller 490. Data recorder 408 may include additional components for communicating with (e.g., transferring data frames, data, etc. to) a processing and/or displaying systems that may be configured to, for example, process images originating from in-vivo imager 412, localization data, and related data. Transceiver 444 may receive (442) the P&O data from in-vivo device 406.

Workstation 430 may include a display or be functionally connected to an external display (402). Controller 490 may transfer location and orientation (P&O) data to workstation 430 for display on, for example, display 402. Workstation 430 may also display information on selectable and/or alternative sets of electromagnets and their calculated electrical currents and their total electrical power, and workstation 430 may, depending on the system's configuration, prompt a user or an operator to manually activate a set of her/his preference. Alternatively, selection of a set of electromagnets and currents may be performed automatically, with workstation 430 only displaying the status of the magnetic system, for example the electromagnets selected for the magnetic maneuvering and their electrical currents. Controller 490 may also send P&O information pertaining to a current P&O of in-vivo device 406, to a magnetic field maneuvering control system (e.g., to controller 340 of FIGS. 3A-3B), which may generate a MMP based on the P&O information it receives from data recorder 408, and, optionally, P&O data pertaining to a new, or desired, P&O.

Figure 5:
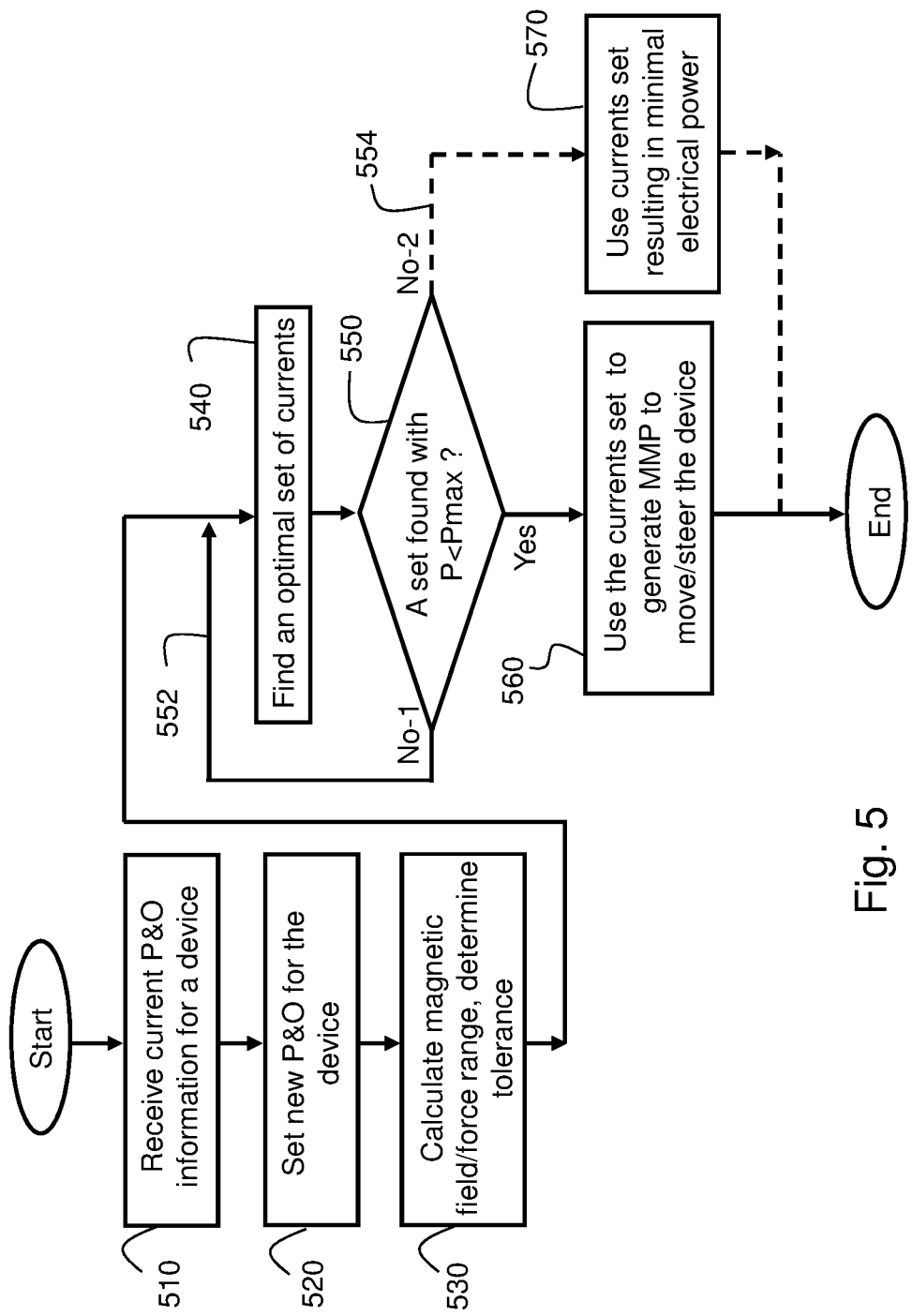
FIG. 5 shows a magnetically maneuvering method according to an example embodiment.

FIG. 5 shows a magnetically maneuvering method according to an example embodiment of the invention. As explained above, controller 340 may be configured to generate a MMP whose magnetic field aligns an in-vivo device in a first direction, and a magnetic gradient (force) whose direction is in a second direction that may differ from the first direction, to thereby change the orientation of the in-vivo device or change its location altogether. Controller 340 may be configured to calculate or select a set of electrical currents for the electromagnets, and provide the calculated/selected currents to the electromagnets in order to obtain (e.g., in order to cause the electromagnets to generate) the wanted or required MMP, as described below. Controller 340 may generate the magnetic field and the magnetic gradient to retain a current location and/or current orientation of the in-vivo device, or to move or rotate the in-vivo device to a wanted location and/or orientation. Controller 340 may select all electromagnets to maneuver the in-vivo device, and individually calculate an electrical current for each electromagnet in order to generate a MMP to maneuver the in-vivo device to the required/next location and, alternatively or additionally, to rotate it to the required/next orientation.

At step 510, a magnetic maneuvering controller (e.g., controller 340 of FIGS. 3A-3B) may receive P&O information related to the current P&O of an in-vivo device; e.g., in-vivo device 360 or 406. A MMP may be determined with respect to a spatial operating region that contains, or that is confined to a limited space that contains the device. Therefore, the current P&O of the device has to be known before a new MMP is calculated or determined. At step 520, a new P&O may be determined/set (e.g., automatically; e.g., by the controller, or manually by a user) for the device.

At step 530, the controller may calculate a magnetic field and a magnetic force for maneuvering the device to the next/new location and/or rotate it to the next/new orientation. There may be cases where navigation accuracy can be compromised. For example, when the in-vivo device is in the small bowel, small deviations or inaccuracies in the location and/or orientation of the device may be acceptable or tolerated, whereas when the device is in the stomach, deviations tolerated in the small bowel (for example) may not be tolerated in the stomach. Therefore, some tolerances/margins, with respect to the electrical parameters and magnetic parameters of the maneuvering system, may be permitted, the permitted tolerances/margins referred to herein as 'constraints'.

At step 540, the controller may select minimum electrical power as an optimization objective and a set of (optimization) constraints and, based on them, determine for the calculated magnetic field and magnetic force (calculated at step 530) a potential set of electrical currents. Applying the potential set of currents to the electromagnets may generate magnetic data or particulars (e.g., magnetic field and magnetic force) that would satisfy the optimization objective (in this example minimum electrical power) under the constraints associated with the optimization objective.

At step 550 it is determined (e.g., by controller 340) whether the set of potential electrical currents calculated at step 540 results in electrical power, P, that is less (lower) than a threshold value, Pmax. If it does (shown as "Yes" at step 550), no other currents sets are searched for by controller 340, and the controller (e.g., controller 340) uses, at step 560, the currents set it found at step 540 to generate a corresponding MMP. However, if the potential set of currents results in electrical power, P, that is greater (higher) than the threshold value, Pmax (shown as "No—1" at step 550), the controller may search for another set of currents (per iteration loop 552), at step 540, for example by changing the optimization objective and/or an optimization constraint. If more than one set of currents have been found by the controller but none of them satisfies condition 550 (shown as "No—2" at step 550), the controller may use the currents set resulting in the minimal electrical power (per branch 554), as shown at step 570.

At step 550 the controller (e.g., controller 340) may execute an optimization procedure to determine which set of electrical currents, if used/applied, would result, for example, in a minimal power consumption, or, according to another example, in a desired magnetic force (e.g., maximum magnetic force, a magnetic force less than the maximum magnetic force, etc.). Each current of a set of electrical currents is associated with a specific electromagnet, and selecting an electrical current also means selecting the associated electromagnet.

The optimization process may be based on, or include use of, formula (1):

$$P = \sum_{i=1}^{n} I_i^2 R_i \qquad (1)$$

where P is the overall electrical power expected to be consumed by all the electromagnets selected for generating the MMP, n is the total number of electromagnets selected for generating the MMP, $I_i$ is the electrical current of electromagnet i (where i=1, 2, ... n), and $R_i$ is the electrical resistance of electromagnet i.

The set of electromagnets actually used/selected to generate a MMP may be those for which P is minimal, for example. Nevertheless, in some cases a less optimal or non-optimal set of electrical currents may be selected, for example in order to obtain a smoother transition of the maneuvered device from one position/orientation to another. The selection of electrical currents may be optimized when the number of linearly independent electromagnets exceeds the number of degrees of freedom (DOFs) required by or involved in the optimization solution.

Figure 6:
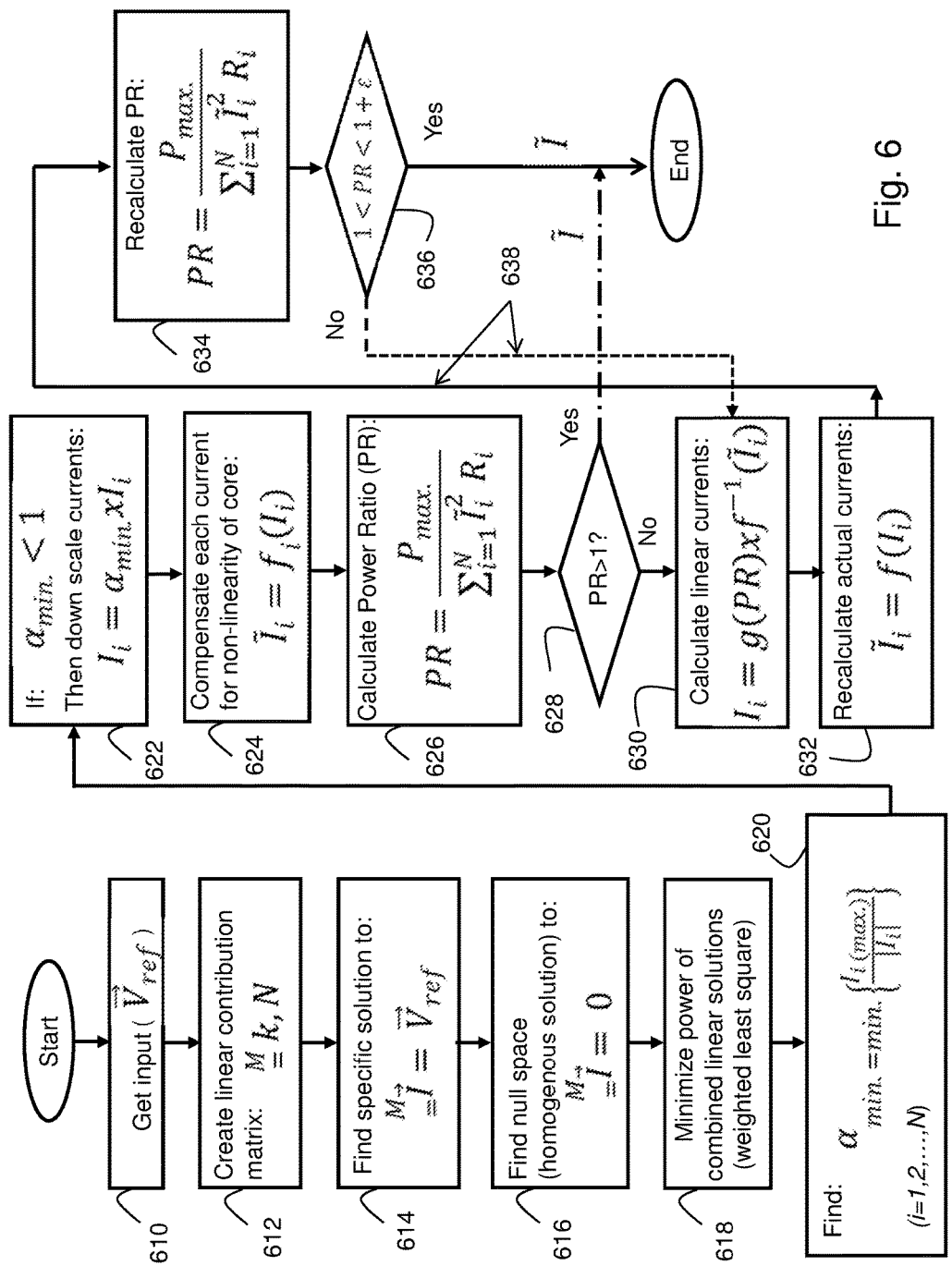
FIG. 6 shows a magnetically maneuvering method according to another example embodiment.

FIG. 6 shows a magnetically maneuvering method according to an example embodiment. At step 610, a specific vector, $\vec{V}_{ref}$, consisting of a combination of elements of $\vec{B}$, $\vec{F}$, $\vec{T}$ (magnetic field ($\vec{B}$), magnetic force ($\vec{F}$) and magnetic torque ($\vec{T}$), respectively) is formed for a location $\vec{P}$ and orientation $\vec{R}$ a magnetically maneuverable capsule is at. The specific vector $\vec{V}_{ref}$ is also a function of N electrical currents respectively flowing in N separate maneuvering electromagnets.

At step 612, a k by N linear 'contribution' matrix, $_=^M k$, N, is created, where k is the length of a target vector $\vec{V}$ and N is the number of maneuvering electromagnets. The target vector, $\vec{V}$, is a vector required to maneuver the capsule to a target or new location and/or orientation. Each element $M_{k,n}$ of matrix M includes a contribution of an electrical current of a known value (e.g., 1 Ampere) in electromagnet #n (n≤N) to element #k of the specific vector $\vec{V}_{ref}$.

At step 614 a particular (private) solution, $\vec{I}_0$, of the equation $_=^M \vec{I} = \vec{V}_{ref}$ is calculated (a specific $\vec{V}_{ref}$ represents a specific combination of $\vec{B}$, $\vec{F}$, $\vec{T}$). The particular solution to the problem may be found by calculating a pseudo-inverse of matrix M, as follows:

$$\vec{I}_p = M^T(MM^T)^{-1}\vec{v} \qquad (2)$$

At step 616 a family (null space, NS) of solutions $\vec{I}_N$ is also calculated by solving the equation $_=^M \vec{I} = 0$. Since the system is linear, these solutions can be combined with the private solution calculated at step 614 in order to obtain all solutions to the electrical currents. The null space (kernel) of M (e.g. $NS_{[N\times(N-K)]}$ satisfying the expression $M \cdot NS \cdot \vec{x} = 0$ may be found for any $\vec{x}_{[(N-k)\times 1]}$) by using formula (3):

$$NS = ker(M) \qquad (3)$$

An electrical current solution that minimizes the required power may be found in the way specified below.

At step 618, after the private solution and null space solutions are calculated, a set of electrical currents that results in minimum electrical power is calculated, for example, by using the "Weighted Least Squares" method. Of all the infinite number of current solutions $\vec{I}_N$ (depending on the number of degrees of freedom of the equation set) that solve the equation $_=^M \vec{I} = \vec{V}_{ref}$, one solution provides a minimal total electrical power. (However, this solution may provide a total electrical power, P, which is smaller or greater than the maximum permissible electrical power, Pmax.) At step 618, this solution is found by using the weighted least squares algorithm, with the arbitrary particular (private) solution ($\vec{I}_0$) found at step 614 and the null space found at step 616 used as parameters.

At step 620 an electrical current correction factor $\alpha_i$ may be calculated for each linear electrical current $I_i$, and, at step 622, the linear electrical currents may all be scaled down using the electrical current correction factor having the minimal value $\alpha_{min}$. Electrical current correction factor, or scale down factor, $\alpha_{min}$ may be calculated using formula (4):

$$\alpha_{min.} = \min\left\{\frac{I_i(\text{max.})}{|I_i|}\right\} \qquad (4)$$

A set of electromagnets that provide minimal total power may be found, for example, by finding $\vec{x}$ that minimizes the overall power. This mathematical problem may be a weighted least square problem with a known solution ($W = w_{i,i}$ is a diagonal weight matrix, where $w_{i,i}$ is the resistance of electromagnet #i):

$$\vec{x} = -(NS^T \cdot W \cdot NS)^{-1} NS^T \cdot W \cdot \vec{I}_p; \qquad (5)$$

The final solution may take the form of $\vec{I}_{linear} = \vec{I}_p + NS \cdot \vec{x}$.

The reason for calculating the correction/scale down factor (and using it, as described below) is that the electrical current (I) in each of the N electromagnets is not permitted to exceed a certain maximum value, $I_{i(max.)}$. However, mathematically, an electromagnet's current calculated for a particular electromagnet may be greater than permitted for this electromagnet. Therefore, at step 620 a scale-down factor, $\alpha$, is calculated for each electromagnet, and a minimum scale-down factor, $\alpha_{min}$, may be selected for scaling down all electrical current of the electromagnets. Scaling down all the electrical currents by using the same scale-down factor, $\alpha$, ensures, on the one hand, that the electrical current actually flowing through/in each electromagnet does not exceed the maximum current permitted for that coil, and, on the other hand, that all the directions of the magnetic fields generated by the involved electromagnets, as well as the spatiotemporal inter relationships between the various magnetic fields, are maintained. (The magnitude of the resulting force applied to the maneuvered device may somewhat decreased due to the down-scaling process.)

Referring again to step 622, it is checked whether $\alpha_{min.} < 1$. If this condition is met (e.g., $\alpha_{min.} < 1$), it means that an electrical current $I_k$ (1≤k≤N) calculated for electromagnet k is greater than the maximum current $I_k(\text{max.})$ permitted for electromagnet k. If this is the case, all the N calculated linear currents are scaled down by multiplying them by $\alpha_{min.}$. Since magnetic characteristics of a magnetic field linearly depend on the electrical currents and electromagnet(s) that generate them, down scaling all the electrical currents by using the same scale-down factor results in maintaining the direction and orientation of the maneuvering magnetic data or particulars (e.g., magnetic field, magnetic force and magnetic torque), though the magnitude of the maneuvering particulars are decreased.

At step 624, the electrical currents (or scaled down currents, if the currents are scaled down) are recalculated in order to compensate them for nonlinearity due to the effect of iron core of the electromagnets, assuming the selected electromagnets, or at least some of them, include an iron core. That is, a maneuvering electromagnet may include an iron core in order to increase the magnetic field, hence the magnetic force, etc. Since iron cores distort the inherent linear behavior of electromagnets, at this step the calculated linear currents, $I_l$, are recalculated (transformed to currents $\tilde{I}_l$) in order to compensate for (factor in) non-linearity caused by such cores. If the recalculated currents meet the other conditions set by the flowchart, they may be used as the actual currents that power/drive the pertinent electromagnets.

At step 626 the total electrical power, P, is calculated for the related electromagnets by using the recalculated, or actual, currents ($\tilde{I}_i$). Then, a power ratio PR, which is a ratio between the calculated total power P and a maximum permissible power Pmax, is calculated in order to determine whether the total power calculated for the related electromagnets meets the power requirement. If the total power meets the power requirement, the related electromagnets are regarded as qualified or eligible candidate electromagnets for generating the MMP.

Accordingly, at step 628 it is checked whether PR>1. If this condition is met (shown as "Yes" at step 628), it means that the actual N electrical currents ($\tilde{I}$) calculated at step 624 result in (amount to) a total power P that is smaller than Pmax.; e.g., in an acceptable total electrical power, in which case the actual N currents ($\tilde{I}$) can be used to power up, or derive, the related N electromagnets to generate the maneuvering magnetic field, or MMP, for which these currents were calculated. However, if PR≤1 (shown as "No" at step 628), it means that the actual electrical currents calculated at step 624 result in (amount to) a total power P that exceeds the maximum allowable total power Pmax., for which reason the electrical currents need to be recalculated (e.g., further scaled down), for example as described below in connection with step 630.

At step 630 the electrical currents are further scaled down as described below. Scaling down electrical currents is beneficially performed in the linear space. Therefore, the actual currents $\tilde{I}_i$ calculated at step 624 are first converted back from the non-linear space to currents in the linear space, by using the conversion function $f^{-1}(\tilde{I}_i)$, and the converted currents are multiplied by a second down-scaling factor g(PR), where PR<1, in order to further scale down the linear currents. It is noted that at this stage the original electrical currents (the linear currents calculated at step 618) are scaled down two times: a first time at step 622 (by using $\alpha_{min}$) to ensure that neither of the electromagnet currents exceeds a maximum current threshold, and a second time at step 630 (by using g(PR), which is referred to herein as the 'power scale-down factor') to ensure that the total electrical power, P, of the related electromagnets do not exceed a maximum power threshold, Pmax. (The smaller g(PR); e.g., the higher the calculated total power P, the more dominant the effect of the power scale-down factor, g(PR), is.)

At step 632 the updated (the 'second time' scaled down) linear electromagnet currents calculated by using the power scale-down factor are converted back to (update) actual currents in a similar way as in step 624, to compensate for the non-linearity effect of the iron cores of the pertinent electromagnets. (Since different electromagnets may have iron cores with different electrical/magnetic characteristics, each coil i may have its own non-linearity compensation, or 'linear-to-actual' current, function $f_i$.)

At step 634 the power ratio (PR) is recalculated in a similar way as in step 626, only at step 634 the PR is calculated using, or for, the updated actual currents ($\tilde{I}_i$) calculated at step 632. At step 636 it is checked whether the updated PR is greater than one and less than one plus epsilon. Similarly to step 628, if the updated PR is greater than one (shown as "Yes" at step 636), it means that the actual N electrical currents ($\tilde{I}$) calculated at step 632 result in (amount to) a total power P that satisfies the power constraint; e.g., that P is smaller than Pmax, hence acceptable. However, another condition is checked at step 636, which is the condition PR<(1+ε) where ε>0, in order to ensure that the total power P is not unnecessarily too small. If the updated PR ratio satisfies both conditions of step 636, the actual N currents ($\tilde{I}$) can be selected to power up, or derive, the related N electromagnets to generate the maneuvering magnetic field, or MMP, for which these currents were calculated. (Epsilon is referred to herein as the 'iteration convergence factor'.)

If the value of PR is less than or equal to one (shown as "No" at step 636), it means that the actual electrical currents calculated at step 632 result in (amount to) a total power P that is still too high (e.g., it still exceeds the maximum allowable total power Pmax) or it is undesirably equal to the power threshold (Pmax). Therefore, the electrical currents need to be further scaled down at step 630 by using the power scale-down factor. Steps 630, 632, 634 and 636 may be performed iteratively (the iteration loop is partly shown at 638) in order to converge the value of PR towards the value one, and some small positive value (epsilon) is used in order to ensure termination of the convergence process. Epsilon (the iteration convergence factor) may be selected to be small enough so that the electromagnets' currents will not be unnecessarily scaled down too much (and the resulting calculated total electrical power P consequently be unnecessarily too small), and, on the other hand, the value of epsilon may be selected to be high enough to ensure termination of the convergence process, hence termination of the iteration loop 638.

If PR>(1+ε) in step 636, this means that the current solution ($\tilde{I}$) was scaled down more than required, which is undesirable because the resulting, or consequent, magnetic force, magnetic torque, magnetic field, etc. would be small with no reason. Therefore, the electrical currents may be scaled down until PR equals one, within the permissible iteration convergence factor (ε).

Figure 7:
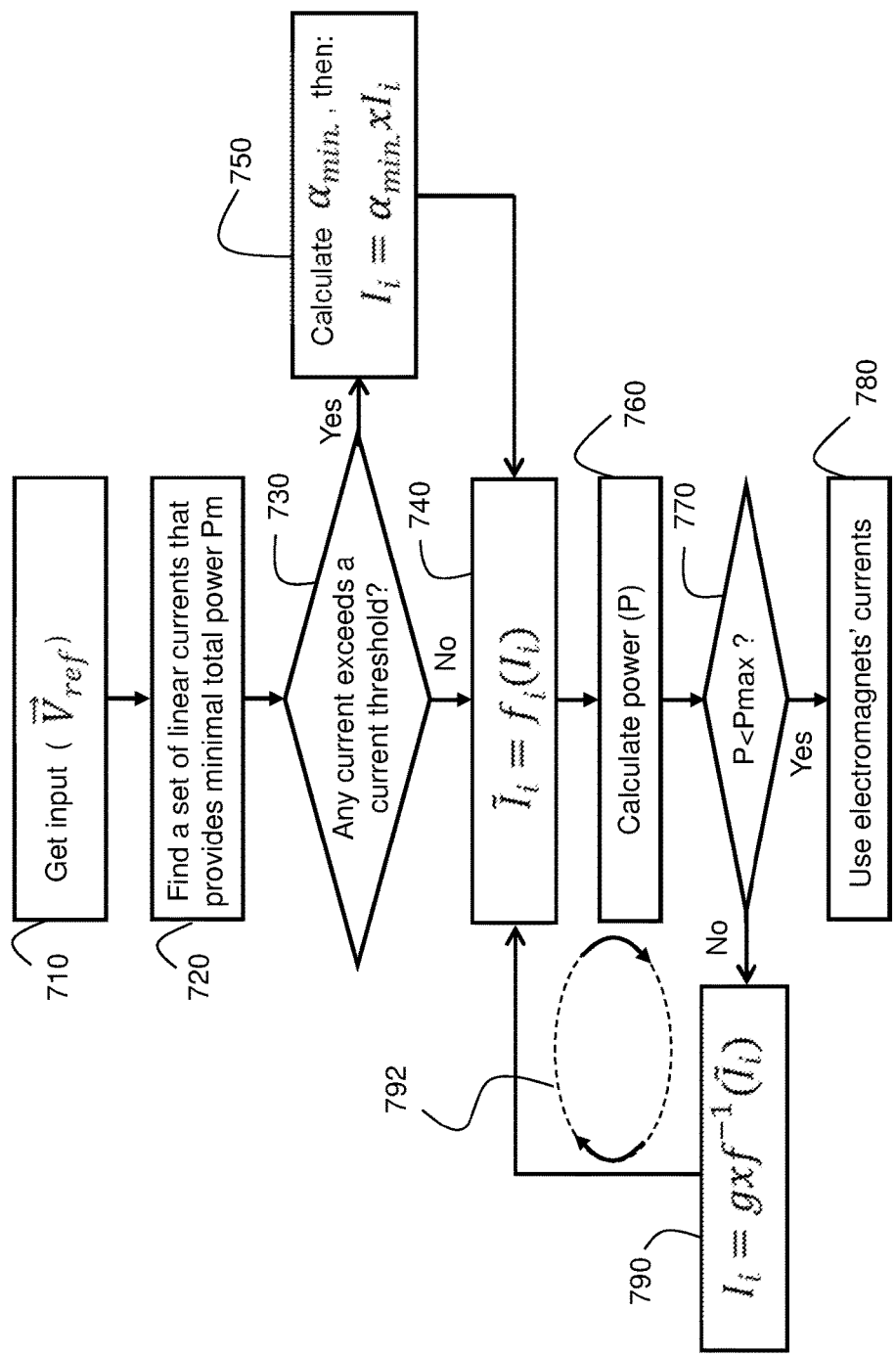
FIG. 7 shows a magnetically maneuvering method according to yet another example embodiment.

FIG. 7 shows a magnetically maneuvering method according to an example embodiment. At step 710, a specific vector, $\vec{V}_{ref}$, similar to specific vector $\vec{V}_{ref}$ of FIG. 6 (at step 610) is formed for (to mathematically represent) a location $\vec{P}$ and orientation $\overline{R}a$ magnetically maneuverable capsule is at, and which is also a function of N electrical currents respectively flowing in N independent maneuvering electromagnets. (The specific vector is a vector required to move the capsule from a location a device is at in a wanted direction and/or to change the orientation of the device to a wanted direction.)

At step 720, a k by N linear contribution matrix similar to the matrix $=^M k, N$ of FIG. 6 (at step 612) is created. Then, a particular (private) solution, $\vec{I}_0$, of the equation $=^M \vec{I} = \vec{V}_{ref}$ (a specific vector $\vec{V}_{ref}$ represents a specific combination of $\vec{B}, \vec{F}, \vec{T}$) and the null space solutions related to the M matrix are calculated, the result of the calculations being a set currents that, if used to drive the pertinent of electromagnets, would generate a MMP that moves the device in the direction and/or rotate it to an orientation as designated or intended by the specific vector $\vec{V}_{ref}$. (The electrical currents calculated at step 720 are referred to as 'linear currents' because these currents are calculated (the currents solution is found) by using a set of linear equations.)

At step 730 it is checked whether any of the linear currents calculated/found at step 720 exceeds a respective maximum current threshold (Imax) (Since the spatial positions of the electromagnets vary and electromagnets may have different electrical/magnetic/physical properties, each electromagnet may have associated with it a different maximum permissible electrical current.) If the maneuvering electromagnets are coreless ('core-free'), the linear currents themselves may be used to activate/drive the maneuvering electromagnets. However, as explained above, if one or more electromagnets include a core, the pertinent linear currents may need to be compensated for a non-linearity artifact that is induced by the core. (Assume that at least some of the electromagnets include an iron core.)

If none of the linear currents exceeds its respective maximum current threshold (shown as "No" at step 730), the linear currents are compensated, at step 740, for a non-linearity effect caused by the respective iron core. (Compensating linear currents for non-linearity effect of the related iron cores result in electrical currents that are referred to herein as 'actual currents'.) However, if at least one of the linear currents found at step 720 exceeds its respective maximum current threshold (shown as "Yes" at step 730), then, at step 750, all the linear currents are scaled down (reduced proportionally), or normalized, by using a same current scaled down factor (CSDF), $\alpha$, before compensation for a non-linearity effects is performed. CSDF $\alpha$ may be calculated, for example, in the way described in connection with step 620 of FIG. 6. Since the linear currents are calculated by using a system of linear equations, scaling down the currents by using the same CSDF maintains linearity of the currents solution, hence of the magnetic properties of the maneuvering magnetic field, or MMP, though the magnitude/strength of the magnetic field (hence the magnetic force and torque) is reduced.

At step 760 the total electrical power, P, of the electromagnets is calculated using the electrical currents calculated at step 740, and at step 770, it is checked whether the total electrical power (P) of the electromagnets is smaller than a predetermined maximum power (Pmax) permitted for the maneuvering system. If it is determined that P is smaller than Pmax (shown at "Yes" at step 770), the electrical currents calculated at step 740 are both regarded as current-wise and power-wise eligible for driving the electromagnets. That is, the electrical current solution found at step 740 provides a set of electrical currents that do not exceed their respective maximum values, and the maneuvering system's power is able to provide the required electrical power. However, if it is determined that P is equal to or greater than Pmax (shown at "No" at step 770), this means that the currents, even though they meet the currents constraints, still result in impermissible total power. Therefore, the electrical currents involved are further scaled down at step 790, this time by using a power scale down factor (PSDF), g. A prerequisite to maintaining linearity of the currents solution after implication of the PSDF is to, first, convert the actual currents found at step 740 back to linear currents, and, then, to scale down the linear currents further using the PSDF (g). Then, the scaled down linear currents calculated at step 790 are compensated, at step 740, for non-linearity effects. The PSDF (g) may be a function of a ratio between Pmax and the actual/total power, P, resulting from the calculated electrical currents, for example, as shown at step 626 and 630 of FIG. 6. The steps 740, 760, 770 and 790 may be iterated, and iteration loop 792 may be terminated when P<Pmax.

Figure 8:
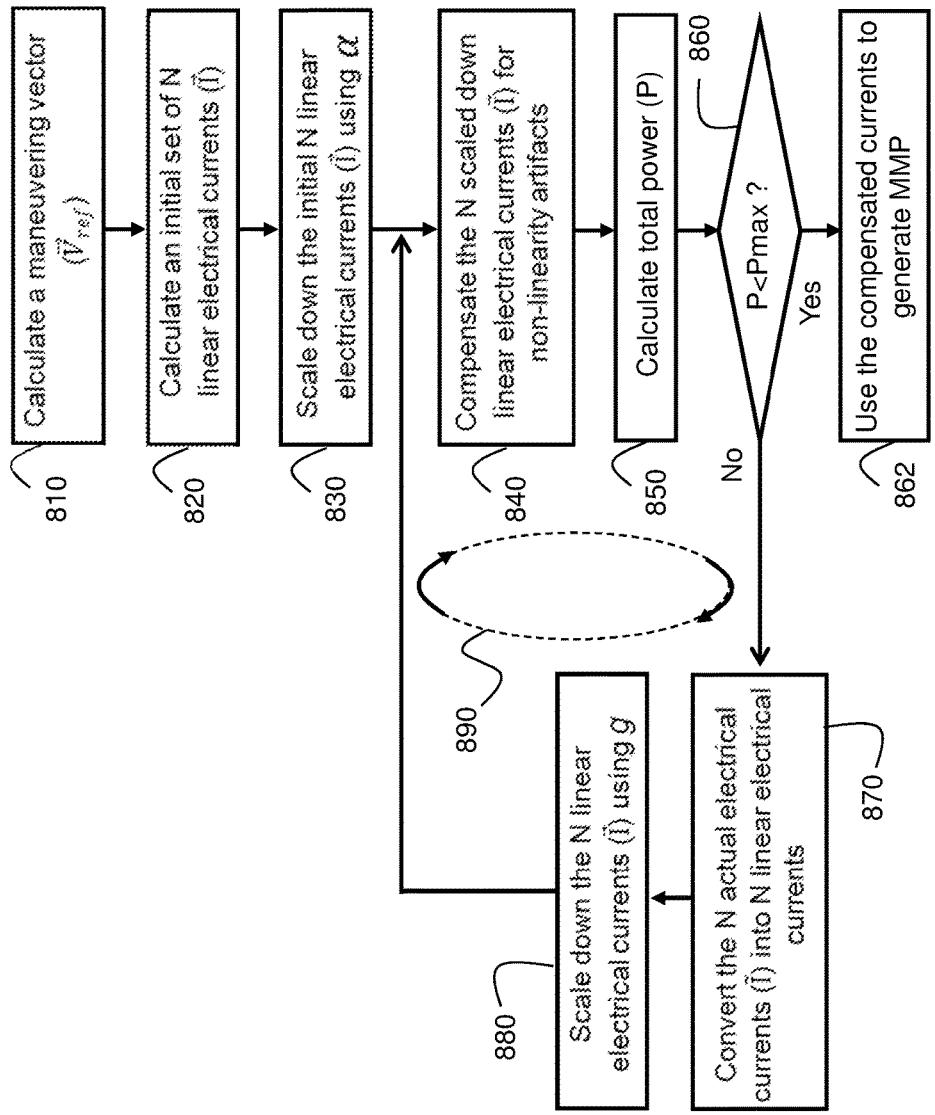
FIG. 8 shows a magnetically maneuvering method according to still another example embodiment.

FIG. 8 shows a magnetically maneuvering method according to another example embodiment. The method may be used to magnetically maneuver an in-vivo device in a GI tract of a subject, by using a magnetic system comprising N electromagnets for generating a maneuvering magnetic field pattern (MMP) for moving the in-vivo device from a location in the GI tract of a subject to another location, or for changing an orientation of the in-vivo device.

At step 810, a controller controlling the magnetic system may calculate a maneuvering vector ($\vec{V}_{ref}$) including a combination of magnetic field data or particulars of a desired or wanted MMP to be generated by a set of m (m≤N) electrical currents respectively passing through/in the m electromagnets.

At step 820, the controller may calculate values of an initial set of m linear electrical currents ($\vec{I}$) that comply with the maneuvering vector ($\vec{V}_{ref}$) and result in minimal total electrical power (Pm). At step 830, the controller may scale down the initial m linear electrical currents ($\vec{I}$) by multiplying them by an electrical current correction factor $\alpha$ (0<$\alpha$≤1). For example, the controller may calculate an electrical current correction factor $\alpha$ for each linear electrical current, and scale down the linear electrical currents using the electrical current correction factor $\alpha$ having the minimal value (e.g., $\alpha_{min}$).

At step 840, the controller may compensate the m scaled down linear electrical currents ($\vec{I}$) for non-linearity artifacts to obtain a set of m actual electrical currents ($\tilde{I}$), and, at step 850, the controller may calculate a total electrical power (P) resulting from the m actual electrical currents ($\tilde{I}$). If, at step 860, the controller determines that the total electrical power (P) is lower than a maximum power (Pmax) threshold (shown as "Yes" at step 860), the controller may, at step 862, generate the maneuvering magnetic pattern (MMP) by using the m actual electrical currents ($\tilde{I}$). However, if the controller determines that the total electrical power (P) is equal to or greater than the maximum power threshold (shown as "No" at step 860), the controller may (i) convert the m actual electrical currents ($\tilde{I}$) into m linear electrical currents, as shown at step 870, (ii) scale down the m linear electrical currents ($\vec{I}$) by multiplying the m linear electrical currents ($\vec{I}$) by a power correction factor g (0<g<1), as shown at step 880, and iteratively perform iteration loop 890 until the total electrical power (P) resulting from the m actual electrical currents is lower than the maximum power (Pmax) threshold. By converting actual currents to linear currents in preparation for the scaling down process the scaling down process scales down the MMP proportionally while maintaining the original directions of the magnetic field, magnetic force and magnetic torque.

Figure 9:
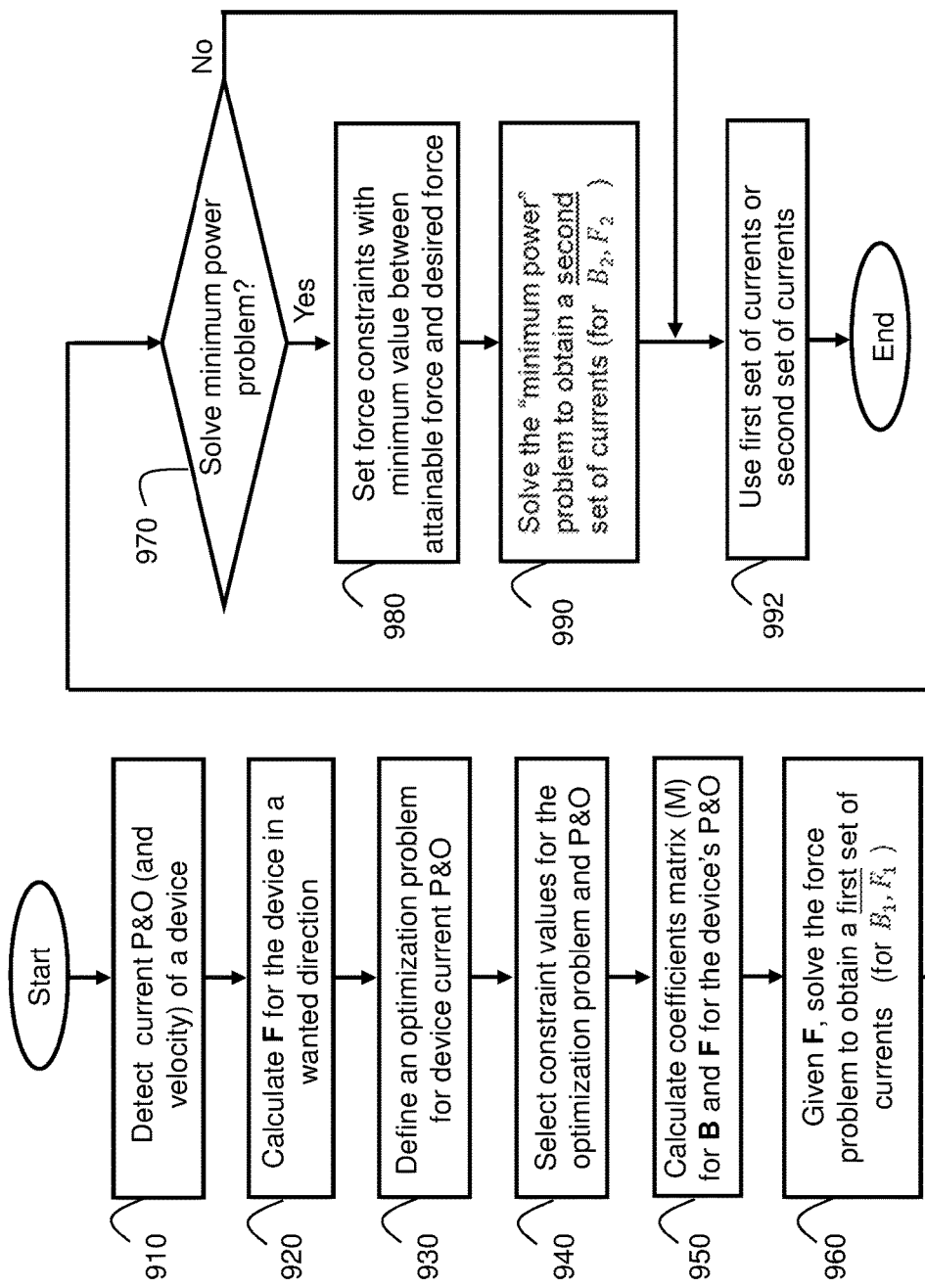
FIG. 9 shows magnetically maneuvering method according to still another example embodiment.

FIG. 9 shows magnetically maneuvering method according to still another example embodiment. At step 910, the current P&O (and optionally the velocity) of a device (e.g., an in-vivo device) are detected, for example by using any off the shelf localization (and, if relevant, velocity) detecting systems suitable for determining the location, orientation (and velocity) of an in-vivo device in the GI tract. At step 920, a magnetic force (F) required (therefore wanted in order) to move the device from its current location in a wanted direction (e.g., 'forward' direction) is calculated. (By 'forward direction' is meant herein in a direction of a longitudinal, or lengthwise, axis of the device.)

At step 930, a magnetic force optimization problem is defined for the device based on the current P&O of the device (and, if desired, velocity). According to some embodiments, the magnetic force (F) calculated at step 920 may depend on (be a function of) a current part or region or location in the GI tract the device is at, and, optionally, on the velocity of the device at that GI part/region. For example, the wanted/required force (F) may change depending on whether the device is in the stomach, in the small bowel, or in the colon, and/or whether the device stands still (e.g., stuck), moves too slow, or moves as expected or as required. For example, if the in-vivo device is, for example, an imaging device, then the orientation (e.g., viewing direction) of the device in the stomach may be a more important factor then the magnetic force applied to the device, while in the small bowel the magnetic force that moves the device may be a more important factor than the orientation of the device. According to another example, it may be required to maintain the device's velocity regardless of the location of the device in the GI tract, but the magnetic force moving the device may change according to the location of the device. The optimization problem may, therefore, be defined according to the required magnetic force (F), or according to a maximum permissible electrical power (P) that the involved electromagnets are designed to operate with.

Accordingly, at step 940, a set of constraint values are set, selected, defined, calculated or otherwise determined for the optimization problem, taking into account the considerations described above (e.g., P&O information). At step 950, coefficients of a matrix (M) are calculated in order to solve the optimization problem. The optimization problem may be solved using the constraints determined at step 940 for the required magnetic field (B) and magnetic force (F).

At step 960 the magnetic force (F) calculated at step 920 for moving the device forward may be used to solve the force optimization problem. The solution to the force optimization problem is a first set of electrical currents that jointly generate the magnetic field gradient required to produce the magnetic force (F) calculated at step 920.

At step 970 it is checked whether there is a need to solve a minimum electrical power problem. If, for example, the magnetic force to be applied to the device is relatively small, there is no need to solve a minimum electrical power problem because minimum electrical power, in such cases, is not an issue. However, if the magnetic force to be applied to the device is relatively high (e.g., it is greater than some force threshold value), then there is room for solving a minimum electrical power problem. Accordingly, if there is no need to solve a minimum power problem (shown as "No" at step 970), the first set of currents calculated at step 960 is used, at step 992, to drive the electromagnets. However, if there is a need to solve a minimum power problem (shown as "Yes" at step 970), force constraints with minimum value between attainable force and desired force is set, at step 980, and, at step 990 the "minimum power" problem is solved in order to obtain a second set of currents, then, at step 992, the second set of currents is used to drive the electromagnets.

According to some embodiments a method for moving an in-vivo device in vivo (e.g., device 360 of FIG. 3A, or device 406 of FIG. 4) may include receiving, by a magnetic maneuvering system operating/driving electromagnets, a first set of magnetic field data (or first data), which may represent a first set of magnetic field particulars, that may be calculated from data that represents a location and orientation of an in-vivo device. (The magnetic maneuvering system may be similar to, include or function like, for example, system 100 of FIG. 1, system 205 of FIG. 2, system 310 of FIG. 3A and system 310' of FIG. 3B.) The method may additionally include selecting, based on the location and orientation of the in-vivo device, one or more optimization objectives from a group consisting of: (i) a minimum difference between a value, or values, of a second set of magnetic field data (or second data), which may represent a second set of magnetic field particulars, and respective value, or values, of the first magnetic field data, and (ii) a minimum electrical power for, or to be consumed by, the electromagnets. The method may additionally include selecting a set of constraints that may be associated with or derived from a selected optimization objective (one or more optimization objectives may be selected) and the first set of magnetic field particulars. The method may additionally include calculating or selecting a set of electrical currents such that the second magnetic field particulars, when generated by providing the calculated or selected set of electrical currents to the electromagnets to form/create a magnetic maneuvering pattern to maneuver the device, satisfy the selected optimization objective(s), and the selected set of constraints is complied with.

Although embodiments of the invention are not limited in this regard, discussions utilizing terms such as, for example, "computing", "calculating" "determining", "analyzing" or the like, may refer to operation(s) and/or process(es) of a computer, a computing system or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence of steps, operations or procedures. Additionally, some of the described method embodiments or elements thereof can occur or be performed at the same point in time.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various maneuvering systems, and to various optimization techniques. Hence the scope of the claims that follow is not limited by the disclosure herein.

The invention claimed is:

1. A method for moving an in-vivo device in vivo, comprising:
   in a magnetic system comprising a number of N electromagnets for generating a maneuvering magnetic field pattern to move a device in vivo,
   (a) receiving data representative of:
      a first set of magnetic field particulars calculated based on data representing a location and orientation of the in-vivo device, and
      a second set of magnetic field particulars to be generated by the electromagnets;
   (b) selecting, based on the location and orientation,
   (b.1) one or more optimization objectives from:
      (i) a minimum difference between a value or values of the second set of magnetic field particulars and respective value or values of the first set of magnetic field particulars, and
      (ii) a minimum electrical power to be consumed by the electromagnets, and
   (b.2) a set of constraints associated with or derived from a selected optimization objective and the first set of magnetic field particulars; and
   (c) providing to the electromagnets a set of electrical currents such that:
      the second set of magnetic field particulars or the minimum electrical power satisfies the selected optimization objective(s), and the selected set of constraints is complied with.

2. The method as in claim 1, wherein selecting a set of constraints comprises selecting one or more constraints from a group consisting of:
   (a) a permissible value, or range, of the magnetic field (B);
   (b) a permissible value, or range, of the magnetic force (F);
   (c) a permissible value, or range, of the magnetic torque (T);
   (d) a permissible value, or range, of a direction ($\alpha$) of the magnetic field;
   (e) a permissible value, or range, of a direction ($\beta$) of the magnetic force; and
   (f) a permissible value or range of a ratio (R) between the magnetic field (B) and the magnetic force (F).

3. The method as in claim 1, wherein the location and orientation data comprises data representing a new location and orientation the in-vivo device is to be maneuvered to.

4. The method as in claim 1, wherein the location and orientation data comprises data representing a current location and a current orientation the in-vivo device is to be maneuvered from.

5. The method as in claim 4, comprising calculating the first set of magnetic field particulars based on (i) the current location and orientation that the in-vivo device is to be maneuvered from, or (ii) a new location and orientation that the in-vivo device is to be maneuvered to, or (iii) both the current and new locations and orientations the in-vivo device is to be maneuvered from and to, respectively.

6. The method as in claim 1, wherein each of the first and second sets of magnetic field particulars comprises a magnetic field, a magnetic force and a magnetic torque.

7. The method as in claim 6, wherein a value of the magnetic force depends on a factor selected from a group of factors consisting of: a location of the device in the gastrointestinal system and a velocity of the device in the gastrointestinal system.

8. The method as in claim 6, wherein a magnetic force applied to the in-vivo device is selected from a group consisting of: (i) a maximum magnetic force ($F_{max}$) and (ii) a magnetic force which is less than the maximum magnetic force.

9. The method as in claim 6, comprising solving a force optimization problem for a calculated magnetic force to obtain a first set of electrical currents for the electromagnets.

10. The method as in claim 9, further comprising solving a minimum electrical power optimization problem to obtain a second set of electrical currents to drive the electromagnets.

11. The method as in claim 9, comprising, depending on: (i) a region of the gastrointestinal tract the in-vivo device is at, or (ii) the magnitude of the magnetic force required to move the in-vivo device, deciding to solve, or to refrain from solving, a minimum electrical power optimization problem to obtain a second set of electrical currents to drive the electromagnets.

12. The method as in claim 9, comprising providing to the electromagnets the first set of electrical currents when no minimum electrical power optimization problem is to be solved, and a second set of electrical currents when the minimum electrical power optimization problem is solved.

13. The method as in claim 1, comprising calculating the set of electrical currents, wherein calculating the set of electrical currents comprises:
   (a) calculating a maneuvering vector ($\vec{V}_{ref}$) including a combination of set of magnetic field particulars of the maneuvering magnetic field pattern;
   (b) calculating an initial set of N linear electrical currents ($\vec{I}$) that complies with the maneuvering vector ($\vec{V}_{ref}$) and results in minimal total electrical power ($P_{min}$);
   (c) scaling down the initial N linear electrical currents ($\vec{I}$) by multiplying the initial N linear electrical currents ($\vec{I}$) by an electrical current correction factor $\alpha$;
   (d) compensating the N scaled down linear electrical currents ($\vec{I}$) for non-linearity artifacts to obtain a set of N compensated electrical currents ($\tilde{I}$);
   (e) if a total electrical power ($P_t$) resulting from the N compensated electrical currents ($\tilde{I}$) is equal to or greater than a maximum power threshold ($P_{max}$) performing,
      (i) converting the N compensated electrical currents ($\tilde{I}$) into N linear electrical currents;
      (ii) multiplying the N linear electrical currents ($\vec{I}$) obtained at step (e)(i) by a power correction factor g (0<g<1), and
      (iii) repeating steps (d) and (e) iteratively until the total electrical power ($P_t$) resulting from the N compensated electrical currents is less than the maximum power ($P_{nax}$) threshold; and
   (f) generating the maneuvering magnetic field pattern using the N compensated electrical currents ($\tilde{I}$) for which the total electrical power is less than the maximum power threshold ($P_{max}$).

14. The method as in claim 13, wherein the value of the electrical current correction factor $\alpha$ is less than one when any current of the initial set of N linear electrical currents ($\vec{I}$) exceeds a predetermined respective maximum threshold value.

15. The method as in claim 13, comprising (i) calculating an electrical current correction factor $\alpha$ for each linear electrical current and (ii) scaling down the N linear electrical currents using the electrical current correction factor $\alpha$ having a minimal value.

16. A method for moving an in-vivo device in vivo, comprising:
- receiving a first set of magnetic field data calculated from data representing a location and orientation of an in-vivo device;
- selecting, based on the location and orientation of the in-vivo device, one or more optimization objectives from a group consisting of: (i) a minimum difference between values of a second set of magnetic field data and values of the first set of magnetic field data, and (ii) a minimum electrical power for a set of N electromagnets;
- selecting a set of constraints associated with an optimization objective and the first set of magnetic field data; and
- providing, to the set of N electromagnets, electrical currents such that:
  - the second set of magnetic field data or the minimum electrical power satisfies the optimization objective(s), and
  - the selected set of constraints is complied with.

17. The method as in claim 16, comprising providing to the set of N electromagnets a first set of electrical currents when the minimum electrical power optimization objective is not selected, and a second set of electrical currents when the minimum electrical power optimization objective is selected.

18. A magnetic system for maneuvering an in-vivo device in a gastrointestinal tract, comprising:
- a number N of electromagnets positioned circularly and forming a plane; and
- a processor to control the electrical currents to the electromagnets, the processor configured to:
- receive data representative of a first set of magnetic field particulars calculated based on data representing a location and orientation of the in-vivo device;
- select, based on the location and orientation, one or more optimization objectives from:
  - (i) a minimum difference between a value or values of a second set of magnetic field particulars to be generated by the electromagnets and respective value or values of the first set of magnetic field particulars, and
  - (ii) a minimum electrical power to be consumed by the electromagnets, and
- select a set of constraints associated with or derived from a selected optimization objective and the first set of magnetic field particulars; and
- provide to the electromagnets a set of electrical currents such that:
  - the second set of magnetic field particulars of the minimum electrical power satisfy the selected optimization objective(s), and
  - the selected set of constraints is complied with.

19. The system as in claim 18, wherein the processor is configured to solve, for a given magnetic force, a magnetic force optimization problem to obtain a first set of electrical currents for the electromagnets, and to solve a minimum electrical power optimization problem to obtain a second set of electrical currents for the electromagnets.

20. The system as in claim 19, wherein the processor is configured to provide to the electromagnets the first set of electrical currents when no minimum electrical power optimization problem is to be solved and the second set of electrical currents when the minimum electrical power optimization problem is solved.

21. The system as in claim 20, wherein the processor is configured to solve, or to refrain from solving, the minimum electrical power optimization problem based on a decision depending on any of: (i) a region of the gastrointestinal tract the in-vivo device is in and (ii) a magnitude of the magnetic force required to move the in-vivo device.

* * * * *